(12) United States Patent
Sparks et al.

(10) Patent No.: US 7,402,730 B1
(45) Date of Patent: Jul. 22, 2008

(54) KNOCKOUT ANIMALS MANIFESTING HYPERLIPIDEMIA

(75) Inventors: Mary Jean Sparks, Magnolia, TX (US); Wenhu Huang, Pittsford, NY (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 0 days.

(21) Appl. No.: 11/347,838

(22) Filed: Feb. 3, 2006

Related U.S. Application Data

(60) Provisional application No. 60/649,509, filed on Feb. 3, 2005.

(51) Int. Cl.
*A01K 67/027* (2006.01)
*A01K 67/00* (2006.01)
*G01N 33/00* (2006.01)
*C12P 21/00* (2006.01)
*C12N 15/00* (2006.01)
*C12N 5/00* (2006.01)
*G01N 33/02* (2006.01)

(52) U.S. Cl. ............... 800/18; 800/3; 800/6; 800/8; 800/21; 435/325

(58) Field of Classification Search ............... None
See application file for complete search history.

(56) References Cited

U.S. PATENT DOCUMENTS

| | | |
|---|---|---|
| 4,179,337 A | 12/1979 | Davis et al. |
| 4,215,051 A | 7/1980 | Schroeder et al. |
| 4,631,211 A | 12/1986 | Houghten |
| 4,689,405 A | 8/1987 | Frank et al. |
| 4,713,326 A | 12/1987 | Dattagupta et al. |
| 4,816,567 A | 3/1989 | Cabilly et al. |
| 4,873,191 A | 10/1989 | Wagner et al. |
| 4,946,778 A | 8/1990 | Ladner et al. |
| 5,260,203 A | 11/1993 | Ladner et al. |
| 5,272,057 A | 12/1993 | Smulson et al. |
| 5,424,186 A | 6/1995 | Fodor et al. |
| 5,445,934 A | 8/1995 | Fodor et al. |
| 5,464,764 A | 11/1995 | Capecchi et al. |
| 5,487,992 A | 1/1996 | Capecchi et al. |
| 5,530,101 A | 6/1996 | Queen et al. |
| 5,556,752 A | 9/1996 | Lockhart et al. |
| 5,585,089 A | 12/1996 | Queen et al. |
| 5,693,761 A | 12/1997 | Queen et al. |
| 5,693,762 A | 12/1997 | Queen et al. |
| 5,700,637 A | 12/1997 | Southern |
| 5,744,305 A | 4/1998 | Fodor et al. |
| 5,766,886 A | 6/1998 | Studnicka et al. |
| 5,789,215 A | 8/1998 | Berns et al. |
| 5,837,458 A | 11/1998 | Minshull et al. |
| 5,869,619 A | 2/1999 | Studnicka |
| 5,877,397 A | 3/1999 | Lonbert et al. |
| 5,968,502 A | 10/1999 | Treco et al. |
| 6,075,181 A | 6/2000 | Kucherlapati et al. |
| 6,114,598 A | 9/2000 | Kucherlapati et al. |
| 6,180,370 B1 | 1/2001 | Queen et al. |
| 6,524,818 B1 | 2/2003 | Harrington et al. |

FOREIGN PATENT DOCUMENTS

| | | |
|---|---|---|
| EP | 0154316 | 9/1985 |
| EP | 0401384 | 12/1990 |
| WO | WO 88/01649 A1 | 3/1988 |
| WO | WO 92/16221 A1 | 10/1992 |
| WO | WO 95/13312 A1 | 5/1995 |
| WO | WO 95/34326 A1 | 12/1995 |
| WO | WO 96/11953 A1 | 4/1996 |
| WO | WO 96/19459 A1 | 6/1996 |
| WO | WO 98/24893 A2 | 6/1998 |
| WO | WO 02/070669 A2 | 9/2002 |

OTHER PUBLICATIONS

Jiao et al., 1990, Metabolism 39:155-60.*
Holschneider et al., 2001, Int. J. Devl. Neuroscience 18:615-618.*
Gerlai et al.,1996, Trends in Neuro Sciences 19:177-181.*
Ioka et. al., 2003, J Biol. Chem. 278:7344-7349.*
Bitter et al, 1987, "Expression and Secretion Vectors for Yeast", Methods in Enzymology 153:516-544.
Blake et al, 1996, "Metal Binding Properties of a Monoclonal Antibody Directed toward Metal-Chelate Complexes", Journal of Biological Chemistry 271:27677-27685.
Boder et al, 2000, "Directed evolution of antibody fragments with monovalent femtomolar antigen-binding affinity", PNAS 97:10701-10705.
Boder et al, 1997, "Yeast surface display for screening combinatorial polypeptide libraries", Nature Biotechnology 15:553-557.
Borrebaeck et al, 1988, "Human monoclonal antibodies produced by primary in vitro immunization of peripheral blood lymphocytes", Proc. Natl. Acad. Sci. USA 85:3995-3999.
Bowie et al., 1991, "A Method to Identify Protein Sequences That Fold into a Known Three-Dimensional Structure", Science 253:164-170.
Brekke et al., 2003, "Therapeutic antibodies for human diseases at the dawn of the twenty-first century", Nature 2:52-62I.
Brenner et al., 1997, "Population statistics of protein structures: lessons from structural classifications", Current Opinion in Structural Biology 7:369-376.
Brommage, 2003, "Validation and calibration of DEXA body composition in mice", Am J Physiol Endocrinol Metab 285:E454-E459.
Carpenter et al., 1971, "Response of dogs to repeated intravenous injection of polyethylene glycol 4000 with notes on excretion and sensitization", Toxicology and Applied Pharmacology 18:35-40.
Chavez et al., 2005, "Acid Ceramidasae Overexpression Prevents the Inhibitory Effects of Saturated Fatty Acids on Insulin Signaling", Journal of Biological Chemistry 280:20148-20153.

(Continued)

*Primary Examiner*—Joesph Woitach
*Assistant Examiner*—Kelaginamane Hiriyanna
(74) *Attorney, Agent, or Firm*—Lance K. Ishimoto

(57) ABSTRACT

Genetically engineered cells and animals are described that incorporate a mutated GHP1 allele. Animals that are homozygous for the mutated GHP1 allele are useful for the production of monoclonal antibodies against GHP1.

2 Claims, No Drawings

OTHER PUBLICATIONS

Chothia et al., 1989, "Conformations on immunoglobulin hypervariable regions", Nature 342::877-883.
Chothia et al., 1987, "Canonical Structures for the Hypervariable Regions of Immunoglobulins", J. Mol. Biol. 196:901-917.
Chou et al., 1979, "Prediction of β-Turns", Biophys. J. Biophysical Society 26:367-384.
Chou et al., 1978, "Empirical Predictions of Protein Conformation", Ann. Res. Biochem. 47:251-276.
Chou et al., 1974, "Conformational Parametaers for Amino Acids in Helical, β-Sheet, and Random Coil Regions Calculated from Proteins", Biochemistry 13:211-222.
Chou et al., 1974, "Prediction of Protein Conformation", Biochemistry 13:222-244.
Chou et al, 1978, "Prediction of the Secondary Structure of Proteins from their Amino Acid Sequence", Adv. Enzymol Relat Area Mol Biol 147:45-148.
Clackson et al, 1991, "Making antibody fragments using phage display libraries", Nature 352:624-628.
Colbere-Garapin et al, 1981, "A New Dominant Hybrid Selective Marker for Higher Eukaryotic Cells", J. Mol. Biol. 150:1-14.
Corrigan et al, 1982, "A Basic microcomputer program for plotting the secondary structure of proteins", Computer Programs in Biomedicine 15:163-168.
Crameri et al., 1996, "Construction and evolution of antibody-phage libraries by DNA shuffling", Nature Medicine 2:100-102.
Drake et al, 2004, "Characterizing high-affinity antigen/antibody complexes by kinetic- and equilibrium-based methods", Analytical Biochemistry 328:35-43.
Fishwild et al., 1996, "High-avidity human IgGK monoclonal antibodies from a novel strain of minilocus transgenic mice", Nature Biotechnology 14:845-851.
Foote et al, 2000, "Breaking the affinity ceiling for antibodies and T cell receptors", PNAS 97:10679-10681.
Goldberg et al., 1993, "Methods for measurement of antibody/antigen affinity based on ELISA and RIA", Current Biology 278-280.
Gordon, 1989, "Transgenic Animals", International Review of Cytology, 115:171-229.
Green, 1999, "Antibody engineering via genetic engineering of the mouse: XenoMouse strains are a vehicle for the facile generation of therapeutic human monoclonal antibodies", Journal of Immunological Methods 231:11-23.
Gribskov et al., 1987, "Profile analysis: Detection of distantly related proteins", Proc. Natl. Acad. Sci. USA 84:4355-4358.
Gribskov et al., 1990, "Profile Analysis", Methods in Enzymology 183:146-159.
Gu et al, 1994, "Deletion of a DNA Polymerase β Gene Segment in T Cells Using Cell Type-Specific Gene Targeting", Science 265:103-106.
Hanes et al., 1998, "Ribosome display efficiently selects and evolves high-affinity antibodies in vitro from immune libraries", Proc. Natl. Acad. Sci. USA 95:14130-14135.
Hoogenboom, 2002, "Overview of Antibody Phage-Display Technology and its Applications", Methods in Molecular Biology 178:1-37.
Hopp et al., 1981, "Prediction of protein antigenic determinants from amino acid sequences", Proc. Natl. Acad. Sci. USA 78:3824-3828.
Hudson et al., 2003, "Engineered antibodies", Nature Medicine 9:129-134.
Inouye et al., 1985, "Up-promoter mutations in the Ipp gene of Escherichia coli", Nucleic Acids Research 13(9):3101-3110.
Ioka et al., 2003, "Expression Cloning and Characterization of a Novel Glycosylphosphatidylinositol-anchored High Density Lipoprotein-binding Proetin, GPI-HBI1", Journal of Biological Chemistry 278:7344-7349.
Irwin, 1968, "Comprehensive Observational Assessment: Ia. A Systematic, Quantitative Procedure for Assessing the Behavioral and Physiologic State of the Mouse", Psychopharmacologia 13:222-257.
Jakobovits, 1995, "Production of fully human antibodies by transgenic mice", Current Opinion in Biotechnology 6:561-566.
Jakobovits et al., 1993, "Germ-line transmission and expression of a human-derived yeast artificial chromosome", Nature 362:255-258.
Janknecht et al, 1991, "Rapid and efficient purification of native histidine-tagged protein expressed by recombinant vaccinia virus", PNAS 88:8972-8976.
Jones, 1997, "Progress in protein structure prediction", Current Opinion in Structural Biology 7:377-387.
Kang et al., 1991, "Antibody redesign by chain shuffling from random combinatorial immunoglobulin libraries", Proc. Natl. Acad. Sci. USA 88:11120-11123.
Karlsson et al., 1991, "Kinetic analysis of monoclonal antibody-antigen interactions with a new biosensor based analytical system", Journal of Immunological Methods 145:229-240.
Krege et al., 1995, "A noninvasive Computerized Tail-Cuff System for Measuring Blood Pressure in Mice", Hypertension 25:1111-1115.
Kohler et al., 1975, "Continuous cultures of fused cells secreting antibody of predefined specificity", Nature 256:495-497.
Kyte et al., 1982, "A Simple Method for Displaying the Hydropathic Character of a Protein", J. Mol. Biol. 157:105-132.
Lakso et al, 1992, "Targeted oncogene activation by site-specific recombination in transgenic mice", Proc. Natl. Acad. Sci. USA 89:6232-6236.
Lavitrano et al, 1989, "Sperm Cells as Vectors for Introducing Foreign DNA into Eggs: Genetic Transformation of Mice", Cell 57:717-723.
Little et al., 2000, "Of mice and men: hybridoma and recombinant antibodies", Immunol. Today 21:364-370.
Lo, 1983, "Transformation by Iontophoretic Microinjection of DNA: Multiple Integrations without Tandem Insertions", Mol. & Cell. Biology 3(10):1803-1814.
Lonberg et al., 1995, "Human Antibodies from Transgenic Mice", Intern. Rev. Immunol. 13:65-93.
Logan et al, 1984, "Adenovirus tripartite leader sequence enhances translation of mRNAs late after infection", Proc. Natl. Acad. Sci. USA 81:3655-3659.
Lowy et al, 1980, "Isolation of Transforming DNA: Cloning the Hamster aprt Gene", Cell 22:817-823.
Malik et al., 1992, "Polyethylene Glycol (PEG)-modified Granulocyte-Macrophage Colony-stimulating Factor (GM-CSF) with Conserved Biological Activity", Exp. Hematol. 20:1028-1035.
Malmqvist, 1993, "Surface plasmon resonance for detection and measurement of antibody-antigen affinity and kinetics", Current Opinion in Immunology 5:282-286.
Marks et al., 1991, "By-passing Immunization Human Antibodies from V-gene Libraries Displaye don Phage", J. Mol. Biol. 222:581-597.
Marks et al., 1992, "By-Passing Immunization: Building High Affinity Human Antibodies by Chain Shuffling", Biotechnology 10:779-783.
Mendez et al., 1997, "Functional transplant of megabase human immunoglobulin loci recapitulates human antibody response in mice", Nature Genetics 15:146-156.
Morrison et al, 1984, "Chimeric human antibody molecules: Mouse antigen-binding domains with human constant region domains", Proc. Natl. Acad. Sci. USA 81:6851-6855.
Moult, 1996, "The current state of the art in protein structure prediction", Current Opinion in Biotechnology 7:422-427.
Mulligan et al., 1981, "Selection for animal cells that express the *Escherichia coli* gene coding for xanthine-guanine phosphoribosyltransferase", Proc. Natl. Acad. Sci. USA 78(4):2072-2076.
Neuberger et al, 1984, "Recombinant antibodies possessing novel effector functions", Nature 312:604-608.
O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527-1531.
Ruther et al, 1983, "Easy identification of cDNA clones", EMBO Journal 2(10):1791-1794.
Santerre et al, 1984, "Expression of prokaryotic genes for hygromycin B and G418 resistance as dominant-selection markers in mouse L cells", Gene 30:147-156.

Sarin et al, 1988, "Inhibition of acquired immunodeficiency syndrome virus by oligodeoxynucleoside methylphosphonates", Proc. Natl. Acad. Sci. USA 85:7448-7451.

Sippl et al., 1996, "Threading thrills and threats", Structure 4:15-19.

Smith et al, 1983, "Molecular Engineering of the *Autographa californica* Nuclear Polyhedrosis Virus Genome: Deletion Mutations within the Polyhedrin Gene", J. Virol. 46(2):584-593.

Stein et al, 1988, "Physiochemical properties of phosphorothioate oligodeoxynucleotides", Nucleic Acids Research 16(8):3209-3221.

Szybalska et al., 1962, "Genetics of Human Cell Lines, IV. DNA-Mediated Heritable Transformation of a Biochemical Trait", Proc. Natl. Acad. Sci. USA 48:2026-2034.

Takeda et al, 1985, "Construction of chimaeric processed immunoglobulin genes containing mouse variable and human constant region sequences", Nature 314:452-454.

Tatusova et al., 1999, "BLAST 2 Sequences, a new tool for comparing protein and nucleotide sequences", FEMS Microbioloty Letters 174:247-250.

Thompson et al, 1989, "Germ Line Transmission and Expression of a Corrected HPRT Gene Produced by Gene Targeting in Embryonic Stem Cells", Cell 56:313-321.

Tomizuka et al., 2000, "Double trans-chromosomic mice: Maintenance of two individual human chromosome fragments containing Ig heavy and K loci and expression of fully human antibodies", PNAS 97:722-727.

Van Der Putten et al, 1985, "Efficient insertion of genes into the mouse germ line via retroviral vectors", Proc. Natl. Acad. Sci. USA 82:6148-6152.

Van Heeke et al, 1989, "Expression of Human Asparagine Synthetase in *Escherichia coli*", J. Biol. Chemistry 264(10):5503-5509.

Wigler et al, 1977, "Transfer of Purified Herpes Virus Thymidine Kinase Gene to Cultured Mouse Cells", Cell 11:223-232.

Wigler et al, 1980, "Transformation of mammalian cells with an amplifiable dominant-acting gene", Proc. Natl. Acad. Sci. USA 77(6):3567-3570.

* cited by examiner

KNOCKOUT ANIMALS MANIFESTING HYPERLIPIDEMIA

The present application claims the benefit of U.S. Provisional Application Ser. No. 60/649,509, which was filed on Feb. 3, 2005.

1. TECHNICAL FIELD

Genetically engineered animals are provided that define the physiological activity of mammalian GPI-anchored HDL binding protein 1 (GHP1).

2. INTRODUCTION

GPI-anchored HDL binding protein 1 (GHP1) is conserved among several mammalian species and belongs to the GPI-anchored lymphocyte differentiation antigen Ly-6 family. Ioka et al. (2003) J. Biol. Chem. 278:7344-7349. In vitro studies indicate that cells engineered to over-express GHP1 bind HDL and that GHP1 appears to mediate selective lipid uptake in cultured cells.

3. SUMMARY OF THE INVENTION

In certain embodiments, mutated cells are described that contain a genetically engineered mutation in the GHP1 locus. In certain embodiments, the mutated cells are an embryonic stem cell line. In certain embodiments, the mutated embryonic stem cells are used to generate mammals having the property of being capable of germline transmission of the genetically engineered GHP1 allele. In certain embodiments, animals homozygous for the mutated GHP1 allele (GHP1 knockout animals) manifest dyslipidemia and are thus disease models for conditions such as, but not limited to atherosclerosis, dyslipidemia, hypertriglyceridemia, acute pancreatitis associated with hypertriglyceridemia, Apo-E deficiency, LPL deficiency or hypoactivity, hypercholesterolemia, gout associated with hypercholesterolemia, xanthomatosis (subcutaneous cholesterol deposits), coronary artery disease (including inflammation associated with coronary artery disease), restenosis, peripheral vascular diseases, and stroke. Certain additional disorders of lipid metabolism include, but are not limited to, disorders related to body weight, such as obesity, metabolic syndrome, and other conditions associated with weight gain, weight loss, maintenance of weight loss, or risk of weight regain following weight loss. Certain exemplary disorders of lipid metabolism include, but are not limited to, related blood sugar disorders, such as diabetes, hypertension, and polycystic ovarian syndrome related to insulin resistance (collectively the above are regarded as GHP1-related disorders).

In certain embodiments, the described GHP1 knockout animals are used to generate antibodies against GHP1. In certain embodiments, the antibodies are monoclonal antibodies that bind to GHP1 (GHP1 antibodies) and stabilize or enhance GHP1 activity in vivo. In certain embodiments, the monoclonal antibody is a mouse monoclonal antibody. In certain embodiments, the monoclonal antibody is a humanized monoclonal antibody. In certain embodiments, the monoclonal antibody is a human monoclonal antibody. In certain embodiments, the monoclonal antibody is an antibody fragment. In certain embodiments, the monoclonal antibody is a scFv fragment. In certain embodiments, the monoclonal antibody is a Fab fragment. In certain embodiments, the monoclonal antibody is a F(ab') fragment. In certain embodiments, the monoclonal antibody is a Fab' fragment.

In certain embodiments the genetically engineered cells are human ES cells, and in certain embodiments the ES cells are murine. In certain additional embodiments, the knockout animals are non-human mammals or knockout mice.

4. DETAILED DESCRIPTION OF VARIOUS EMBODIMENTS

It is to be understood that both the foregoing general description and the following detailed description are exemplary and explanatory only and are not restrictive of the invention, as claimed.

In this application, the use of the singular includes the plural unless specifically stated otherwise. In this application, the word "a" or "an" means "at least one" unless specifically stated otherwise. In this application, the use of "or" means "and/or" unless stated otherwise. Furthermore, the use of the term "including," as well as other forms, such as "includes" and "included," is not limiting. Also, terms such as "element" or "component" encompass both elements or components comprising one unit and elements or components that comprise more than one unit unless specifically stated otherwise.

The section headings used herein are for organizational purposes only and are not to be construed as limiting the subject matter described.

4.1. CERTAIN DEFINITIONS

The terms "polypeptide," "peptide," and "protein" are used interchangeably herein to refer to a polymer of amino acid residues. The terms apply to amino acid polymers containing naturally occurring amino acids as well as amino acid polymers in which one or more amino acid residues is an artificial chemical analogue of a corresponding naturally occurring amino acid. The amino acid polymers can be of any length.

The term "antibody," as used herein, refers to an intact antibody or a fragment of an antibody that competes with the intact antibody for antigen binding. Antibody fragments include, but are not limited to, Fab, Fab', F(ab')2, Fv, scFv, Fd, diabodies, and other antibody fragments that retain at least a portion of the variable region of an intact antibody. See, e.g., Hudson et al. (2003) Nature Med. 9:129-134. In certain embodiments, antibody fragments are produced by enzymatic or chemical cleavage of intact antibodies. In certain embodiments, antibody fragments are produced by recombinant DNA techniques.

The term "native polypeptide" refers to a naturally occurring polypeptide. The term "native antibody" refers to a naturally occurring antibody.

The term "monoclonal antibody" refers to an antibody from a substantially homogeneous population of antibodies that specifically bind to the same epitope. In certain embodiments, a monoclonal antibody is secreted by a hybridoma. In certain such embodiments, a hybridoma is produced according to certain methods known to those skilled in the art. See, e.g., Kohler and Milstein (1975) Nature, 256:495-499). In certain embodiments, a monoclonal antibody is produced using recombinant DNA methods (see, e.g., U.S. Pat. No. 4,816,567). In certain embodiments, a monoclonal antibody refers to an antibody fragment isolated from a phage display library (see, e.g., Clackson et al. (1991) Nature 352:624-628, and Marks et al. (1991) J. Mol. Biol. 222:581-597). For various other monoclonal antibody production techniques, see, e.g., Harlow and Lane (1988) Antibodies: A Laboratory Manual (Cold Spring Harbor Laboratory, Cold Spring Harbor, N.Y.).

A "chimeric" antibody refers to an antibody made up of components from at least two different sources. In certain embodiments, a chimeric antibody comprises a portion of an antibody from a first species fused to another molecule, e.g., a portion of an antibody from a second species. In certain such embodiments, a chimeric antibody comprises a portion of an antibody from a non-human animal fused to a portion of an antibody from a human. In certain such embodiments, a chimeric antibody comprises all or a portion of a variable region of an antibody from a non-human animal fused to a constant region of an antibody from a human.

A "humanized" antibody refers to a non-human antibody that has been modified so that it more closely matches (in amino acid sequence) a human antibody. A humanized antibody is thus a type of chimeric antibody. In certain embodiments, amino acid residues outside of the antigen binding residues of the variable region of the non-human antibody are modified. In certain embodiments, a humanized antibody is constructed by replacing all or a portion of a complementarity determining region (CDR) of a human antibody with all or a portion of a CDR from another antibody, such as a non-human antibody, having the desired antigen binding specificity. In certain embodiments, a humanized antibody comprises variable regions in which all or substantially all of the CDRs correspond to CDRs of a non-human antibody and all or substantially all of the FRs correspond to FRs of a human antibody. In certain such embodiments, a humanized antibody further comprises a constant region (Fc) of a human antibody.

The term "human antibody" refers to a monoclonal antibody derived from antibody sequences of human origin. The term is not limited by the manner in which the antibodies are made. For example, in various embodiments, a human antibody may be made in a transgenic mouse, by phage display, by human B-lymphocytes, or by recombinant methods.

The term "neutralizing antibody" or "antibody that neutralizes" refers to an antibody that reduces at least one activity of a polypeptide comprising the epitope to which the antibody specifically binds. In certain embodiments, a neutralizing antibody reduces an activity in vitro. In certain embodiments, a neutralizing antibody reduces an activity in vivo.

The term "antigen-binding site" refers to a portion of an antibody capable of specifically binding an antigen. In certain embodiments, an antigen-binding site is provided by one or more antibody variable regions.

The term "epitope" refers to any polypeptide determinant capable of specifically binding to an immunoglobulin or a T-cell receptor. In certain embodiments, an epitope is a region of an antigen that is specifically bound by an antibody. In certain embodiments, an epitope may include chemically active surface groupings of molecules such as amino acids, sugar side chains, phosphoryl, or sulfonyl groups. In certain embodiments, an epitope may have specific three dimensional structural characteristics (e.g., a "conformational" epitope) and/or specific charge characteristics.

An epitope is defined as "the same" as another epitope if a particular antibody specifically binds to both epitopes. In certain embodiments, polypeptides having different primary amino acid sequences may comprise epitopes that are the same. In certain embodiments, epitopes that are the same may have different primary amino acid sequences. Different antibodies are said to bind to the same epitope if they compete for specific binding to that epitope.

An antibody "selectively binds" an antigen when it preferentially recognizes the antigen in a complex mixture of proteins and/or macromolecules. In certain embodiments, an antibody comprises an antigen-binding site that specifically binds to a particular epitope. In certain such embodiments, the antibody is capable of binding different antigens so long as the different antigens comprise that particular epitope. In certain instances, for example, homologous proteins from different species may comprise the same epitope. In certain embodiments, an antibody is said to specifically bind an antigen when the dissociation constant ($K_D$) is =1 µM, in certain embodiments, when the dissociation constant is =100 nM, and in certain embodiments, when the dissociation constant is =10 nM.

The term "GHP1" refers to a GPI-anchored HDL binding protein 1 from any vertebrate or mammalian source, including, but not limited to, human, bovine, chicken, rodent, mouse, rat, porcine, ovine, primate, monkey, and guinea pig, unless specified otherwise. The term also refers to fragments and variants of native GHP1 that maintain at least one in vivo or in vitro activity of a native GHP1. The term encompasses full-length unprocessed precursor forms of GHP1 as well as mature forms resulting from post-translational cleavage of the signal peptide and forms resulting from proteolytic processing or other post-translational modifications. The amino acid sequence of mouse GHP1 is provided in GENBANK accession no. Q9D1N2 (nucleotide accession no. XM_128001. The amino acid sequence of a full-length human GHP1 is described in GENBANK accession no. Q6P3T2 (nucleotide accession no. NM_178172), and PCT applications nos. WO2001012776, WO2001132676, and WO2002070669 all of which are herein incorporated by reference.

The term "GHP1 nucleotide" refers to a nucleic acid encoding GHP1.

The term "agent" refers to a chemical compound, a mixture of chemical compounds, a biological macromolecule, or an extract made from biological materials.

The term "GHP1 antagonist" refers to an agent that reduces an activity of GHP1.

The term "GHP1 agonist" refers to an agent that increases an activity of GHP1.

The term "patient" includes human and animal subjects.

A "fragment" of a reference polypeptide refers to a contiguous stretch of amino acids from any portion of the reference polypeptide. A fragment may be of any length that is less than the length of the reference polypeptide.

A "variant" of a reference polypeptide refers to a polypeptide having one or more amino acid substitutions, deletions, or insertions relative to the reference polypeptide.

A "conservative" amino acid substitution refers to the substitution of an amino acid in a polypeptide with another amino acid having similar properties, such as size or charge. In certain embodiments, a polypeptide comprising a conservative amino acid substitution maintains at least one activity of the unsubstituted polypeptide. A conservative amino acid substitution can encompass non-naturally occurring amino acid residues, which are typically incorporated by chemical peptide synthesis rather than by synthesis in biological systems. These include, but are not limited to, peptidomimetics and other reversed or inverted forms of amino acid moieties.

Naturally occurring residues may be divided into classes based on common side chain properties:
1) hydrophobic: norleucine, Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

For example, non-conservative substitutions may involve the exchange of a member of one of these classes for a member from another class. Such substituted residues can be introduced into regions of a human antibody that are homologous with non-human antibodies, or into the non-homologous regions of the molecule.

In making substitutions, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein, in certain instances, is understood in the art. Kyte et al., J. Mol. Biol., 157:105-131 (1982). It is known that in certain instances, certain amino acids can be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included. One may also identify epitopes from primary amino acid sequences on the basis of hydrophilicity. These regions are also referred to as "epitopic core regions."

Exemplary amino acid substitutions are set forth in Table 1.

TABLE 1

| Amino Acid Substitutions | |
| --- | --- |
| Original Residue | Exemplary Substitutes |
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala, Phe, Norleucine |

TABLE 1-continued

| Amino Acid Substitutions | |
| --- | --- |
| Original Residue | Exemplary Substitutes |
| Leu | Norleucine, Ile, Val, Met, Ala, Phe |
| Lys | Arg, 1,4 Diamino-buytric Acid, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala, Norlecuine |

A skilled artisan will be able to determine suitable variants of a polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure.

Additionally, in certain embodiments, one skilled in the art can review structure-function studies identifying residues in similar polypeptides that are important for activity or structure. In view of such a comparison, in certain embodiments, one can predict the importance of amino acid residues in a protein that correspond to amino acid residues which are important for activity or structure in similar proteins. In certain embodiments, one skilled in the art may opt for chemically similar amino acid substitutions for such predicted important amino acid residues.

In certain embodiments, one skilled in the art can also analyze the three-dimensional structure and amino acid sequence in relation to that structure in similar polypeptides. In certain embodiments, in view of such information, one skilled in the art may predict the alignment of amino acid residues of an antibody with respect to its three dimensional structure. In certain embodiments, one skilled in the art may choose not to make radical changes to amino acid residues predicted to be on the surface of the protein, since such residues may be involved in important interactions with other molecules. Moreover, in certain embodiments, one skilled in the art may generate test variants containing a single amino acid substitution at each desired amino acid residue. In certain embodiments, the variants can then be screened using activity assays known to those skilled in the art. In certain embodiments, such variants could be used to gather information about suitable variants. For example, in certain embodiments, if one discovered that a change to a particular amino acid residue resulted in destroyed, undesirably reduced, or unsuitable activity, variants with such a change may be avoided. In other words, in certain embodiments, based on information gathered from such routine experiments, one skilled in the art can readily determine the amino acids where further substitutions should be avoided either alone or in combination with other mutations.

A number of scientific publications have been devoted to the prediction of secondary structure. See, e.g., Moult J., Curr. Op. in Biotech., 7(4):422-427 (1996), Chou et al., Biochemistry, 13(2):222-245 (1974); Chou et al., Biochemistry, 113(2):211-222 (1974); Chou et al., Adv. Enzymol. Relat. Areas Mol. Biol., 47:45-148 (1978); Chou et al., Ann. Rev. Biochem., 47:251-276 and Chou et al., Biophys. J., 26:367-384 (1979). Moreover, computer programs are currently available to assist with predicting secondary structure. One method of predicting secondary structure is based upon homology modeling. For example, two polypeptides or proteins that have a sequence identity of greater than 30%, or similarity greater than 40% often have similar structural topologies. The growth of the protein structural database (PDB) has provided enhanced predictability of secondary structure, including the potential number of folds within a polypeptide's structure. See, e.g., Holm et al., Nucl. Acid. Res., 27(1):244-247 (1999). It has been suggested (Brenner et al., Curr. Op. Struct. Biol., 7(3):369-376 (1997)) that there are a limited number of folds in a given polypeptide or protein and that once a critical number of structures have been resolved, structural prediction will become dramatically more accurate.

Additional methods of predicting secondary structure include "threading" (see, e.g., Jones, D., Curr. Opin. Struct. Biol., 7(3):377-87 (1997); Sippl et al., Structure, 4(1):15-19 (1996)), "profile analysis" (see, e.g., Bowie et al., Science, 253:164-170 (1991); Gribskov et al., Meth. Enzym., 183: 146-159 (1990); Gribskov et al., Proc. Nat. Acad. Sci., 84(13):4355-4358 (1987)), and "evolutionary linkage" (see, e.g., Holm et al., Nucl. Acid. Res., 27(1):244-247 (1999), and Brenner et al., Curr. Op. Struct. Biol., 7(3):369-376 (1997)).

In certain embodiments, a variant of a reference antibody includes a glycosylation variant wherein the number and/or type of glycosylation sites have been altered relative to the amino acid sequence of the reference antibody. In certain embodiments, a variant of a polypeptide comprises a greater or a lesser number of N-linked glycosylation sites relative to a native polypeptide. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. In certain embodiments, a rearrangement of N-linked carbohydrate chains is provided, wherein one or more N-linked glycosylation sites (typically those that are naturally occurring) are eliminated and one or more new N-linked sites are created. Exemplary antibody variants include cysteine variants wherein one or more cysteine residues are deleted from or substituted for another amino acid (e.g., serine) relative to the amino acid sequence of the reference antibody. In certain embodiments, cysteine variants may be useful when antibodies must be refolded into a biologically active conformation such as after the isolation of insoluble inclusion bodies. In certain embodiments, cysteine variants have fewer cysteine residues than the native polypeptide. In certain embodiments, cysteine variants have an even number of cysteine residues to minimize interactions resulting from unpaired cysteines.

According to certain embodiments, amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physiochemical or functional properties on such polypeptides. According to certain embodiments, single or multiple amino acid substitutions (in certain embodiments, conservative amino acid substitutions) may be made in a naturally-occurring sequence (in certain embodiments, in the portion of the polypeptide outside the domain(s) forming intermolecular contacts). In certain embodiments, a conservative amino acid substitution typically may not substantially change the structural characteristics of the reference sequence (e.g., in certain embodiments, a replacement amino acid should not tend to break a helix that occurs in the reference sequence, or disrupt other types of secondary structure that characterizes the reference sequence). Examples of certain art-recognized polypeptide secondary and tertiary structures are described, for example, in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

"Percent identity" or "% identity," with reference to nucleic acid sequences, refers to the percentage of identical nucleotides between at least two polynucleotide sequences aligned using the Basic Local Alignment Search Tool (BLAST) engine. See Tatusova et al. (1999) FEMS Microbiol Lett. 174:247-250. The BLAST engine (version 2.2.10) is provided to the public by the National Center for Biotechnology Information (NCBI), Bethesda, Md. To align two polynucleotide sequences, the "Blast 2 Sequences" tool is used, which employs the "blastn" program with parameters set at default values as follows:

Matrix: not applicable
Reward for match: 1
Penalty for mismatch: −2
Open gap: 5 penalties
Extension gap: 2 penalties
Gap_x dropoff: 50
Expect: 10.0
Word size: 11
Filter: on "Percent identity" or "% identity," with reference to polypeptide sequences, refers to the percentage of identical amino acids between at least two polypeptide sequences aligned using the Basic Local Alignment Search Tool (BLAST) engine. See Tatusova et al. (1999) FEMS Microbiol Lett. 174:247-250. The BLAST engine (version 2.2.10) is provided to the public by the National Center for Biotechnology Information (NCBI), Bethesda, Md. To align two polypeptide sequences, the "Blast 2 Sequences" tool is used, which employs the "blastp" program with parameters set at default values as follows:

Matrix: BLOSUM62
Open gap: 11 penalties
Extension gap: 1 penalty
Gap_x dropoff: 50
Expect: 10.0
Word size: 3
Filter: on The term "effective dose" or "effective amount" refers to an amount of an agent, e.g., a antibody or GHP1 product, that results in the reduction of symptoms in a patient or results in a desired biological outcome. In certain embodiments, an effective dose or effective amount is sufficient to reduce at least one activity of GHP1 or reduce, reverse, delay the progression of, at least one symptom associated with dyslipidemia. In certain embodiments, an effective dose or effective amount is determined as described below.

The term "treatment" encompasses both therapeutic and prophylactic/preventative measures unless otherwise indicated. Those in need of treatment include, but are not limited to, individuals already having a particular condition or disorder as well as individuals who are at risk of acquiring a particular condition or disorder (e.g., those needing prophylactic/preventative measures). The term "treating" refers to administering an agent to a patient for therapeutic and/or prophylactic/preventative purposes.

A "therapeutic agent" refers to an agent that may be administered in vivo to bring about a therapeutic and/or prophylactic/preventative effect.

A "therapeutic antibody" refers to an antibody that may be administered in vivo to bring about a therapeutic and/or prophylactic/preventative effect.

The terms "isolated nucleic acid" and "isolated polynucleotide" are used interchangeably and refer to a polynucleotide of genomic, cDNA, or synthetic origin or some combination thereof. An "isolated polynucleotide" (1) is not associated with all or a portion of a polynucleotide in which the "isolated polynucleotide" is found in nature, (2) is linked to a polynucleotide to which it is not linked in nature, or (3) does not occur in nature as part of a larger sequence.

4.2. STRUCTURE OF NATIVE ANTIBODIES AND CERTAIN ANTIBODY FRAGMENTS

A native antibody typically has a tetrameric structure. A tetramer typically comprises two identical pairs of polypeptide chains, each pair having one light chain (in certain embodiments, about 25 kDa) and one heavy chain (in certain embodiments, about 50-70 kDa). In a native antibody, a heavy chain comprises a variable region, VH, and three constant regions, $C_H1$, $C_H2$, and $C_H3$. The $V_H$ domain is at the amino-terminus of the heavy chain, and the $C_H3$ domain is at the carboxy-terminus. In a native antibody, a light chain comprises a variable region, $V_L$, and a constant region, $C_L$. The variable region of the light chain is at the amino-terminus of the light chain. In a native antibody, the variable regions of each light/heavy chain pair typically form the antigen binding site. The constant regions are typically responsible for effector function.

Native human light chains are typically classified as kappa and lambda light chains. Native human heavy chains are typically classified as mu, delta, gamma, alpha, or epsilon, and define the antibody's isotype as IgM, IgD, IgG, IgA, and IgE, respectively. IgG has subclasses, including, but not limited to, IgG1, IgG2, IgG3, and IgG4. IgM has subclasses including, but not limited to, IgM1 and IgM2. IgA has subclasses including, but not limited to, IgA1 and IgA2. Within native human light and heavy chains, the variable and constant regions are typically joined by a "J" region of about 12 or more amino acids, with the heavy chain also including a "D" region of about 10 more amino acids. See, e.g., Fundamental Immunology (1989) ch. 7 (Paul, W., ed., 2nd ed. Raven Press, N.Y.).

In a native antibody, the variable regions typically exhibit the same general structure in which relatively conserved framework regions (FRs) are joined by three hypervariable regions, also called complementarity determining regions (CDRs). The CDRs from the two chains of each pair typically are aligned by the framework regions, which may enable binding to a specific epitope. From N-terminus to C-terminus, both light and heavy chain variable regions typically comprise the domains FR1, CDR1, FR2, CDR2, FR3, CDR3 and FR4. The CDRs on the heavy chain are referred to as H1, H2, and H3, while the CDRs on the light chain are referred to as L1, L2, and L3. Typically, CDR3 is the greatest source of molecular diversity within the antigen-binding site. H3, for example, in certain instances, can be as short as two amino acid residues or greater than 26. The assignment of amino acids to each domain is typically in accordance with the definitions of Kabat et al. (1991) Sequences of Proteins of Immunological Interest (National Institutes of Health, Publication No. 91-3242, vols. 1-3, Bethesda, Md.); Chothia & Lesk J. Mol. Biol. 196:901-917 (1987); or Chothia et al. Nature 342:878-883 (1989). In the present application, the term "CDR" refers to a CDR from either the light or heavy chain, unless otherwise specified.

A "Fab" fragment comprises one light chain and the CH1 and variable region of one heavy chain. The heavy chain of a Fab molecule cannot form a disulfide bond with another heavy chain molecule. A "Fab'" fragment comprises one light chain and one heavy chain that comprises additional constant region, extending between the $C_H1$ and $C_H2$ domains. An interchain disulfide bond can be formed between two heavy chains of a Fab' fragment to form a "F(ab')$_2$" molecule.

An "Fv" fragment comprises the variable regions from both the heavy and light chains, but lacks the constant regions. A single-chain Fv (scFv) fragment comprises heavy and light chain variable regions connected by a flexible linker to form a single polypeptide chain with an antigen-binding region. Exemplary single chain antibodies are discussed in detail in WO 88/01649 and U.S. Pat. Nos. 4,946,778 and 5,260,203. In certain instances, a single variable region (one-half of an Fv) may have the ability to recognize and bind antigen, albeit with lower affinity than the Fv.

4.3. CERTAIN ANTIBODIES

In certain embodiments, monoclonal antibodies that selectively bind to GHP1 are provided. In certain such embodiments, the monoclonal antibodies are neutralizing monoclonal antibodies that reduce at least one activity of GHP1 in vivo and/or in vitro, and in certain embodiments the monoclonal antibodies promote or stabilize GHP1 binding of its ligand in vitro and in vivo.

4.3.1. Chimerized and Humanized Monoclonal Antibodies

In certain embodiments, non-human antibodies are chimerized. In certain embodiments, mouse monoclonal antibodies that specifically bind human GHP1 are chimerized. Certain exemplary methods for making chimeric antibodies are provided, for example, in Morrison et al. (1984) Proc. Nat'l Acad. Sci. USA 81:6851-6855; Neuberger et al. (1984) Nature 312:604-608; Takeda et al. (1985) Nature 314:452-454; and U.S. Pat. Nos. 6,075,181 and 5,877,397.

In certain embodiments, non-human antibodies are "humanized." In certain embodiments, mouse monoclonal antibodies that specifically bind human GHP1 are humanized. In certain embodiments, mouse monoclonal antibodies raised against mouse GHP1, but which specifically bind (i.e., cross react) with human GHP1, are humanized. In certain embodiments, humanized antibodies retain their binding specificity and have reduced immunogenicity (e.g., reduced human anti-mouse antibody (HAMA) response) when administered to a human. In certain embodiments, humanization is achieved by methods including, but not limited to, CDR grafting or human engineering, as described in detail below.

In certain embodiments of humanized antibodies, one or more complementarity determining regions (CDRs) from the light and heavy chain variable regions of an antibody with the desired binding specificity (the "donor" antibody) are grafted onto human framework regions (FRs) in an "acceptor" antibody. Exemplary CDR grafting is described, e.g., in U.S. Pat. Nos. 6,180,370, 5,693,762, 5,693,761, 5,585,089, and 5,530, 101; Queen et al. (1989) Proc. Nat'l Acad. Sci. USA 86:10029-10033. In certain embodiments, one or more CDRs from the light and heavy chain variable regions are grafted onto consensus human FRs in an acceptor antibody. To create consensus human FRs, in certain embodiments, FRs from several human heavy chain or light chain amino acid sequences are aligned to identify a consensus amino acid sequence.

In certain embodiments, certain FR amino acids in the acceptor antibody are replaced with FR amino acids from the donor antibody. In certain such embodiments, FR amino acids from the donor antibody are amino acids that contribute to the affinity of the donor antibody for the target antigen. See, e.g., in U.S. Pat. Nos. 6,180,370, 5,693,762, 5,693,761, 5,585,089, and 5,530,101; Queen et al. (1989) Proc. Nat'l Acad. Sci. USA 86:10029-10033. In certain embodiments, computer programs are used for modeling donor and/or acceptor antibodies to identify residues that are likely to be involved in binding antigen and/or to contribute to the structure of the antigen binding site, thus assisting in the selection of residues, such as FR residues, to be replaced in the donor antibody.

In certain embodiments, CDRs from a donor antibody are grafted onto an acceptor antibody comprising a human constant region. In certain such embodiments; FRs are also grafted onto the acceptor. In certain embodiments, CDRs from a donor antibody are derived from a single chain Fv antibody. In certain embodiments, FRs from a donor antibody are derived from a single chain Fv antibody. In certain embodiments, grafted CDRs in a humanized antibody are further modified (e.g., by amino acid substitutions, deletions, or insertions) to increase the affinity of the humanized antibody for the target antigen. In certain embodiments, grafted FRs in a humanized antibody are further modified (e.g., by amino acid substitutions, deletions, or insertions) to increase the affinity of the humanized antibody for the target antigen.

In certain embodiments, non-human antibodies can be rendered more suitable for human therapeutic use via a "human engineering" method. See, e.g., U.S. Pat. Nos. 5,766,886 and 5,869,619. In certain embodiments of human engineering, information on the structure of antibody variable domains (e.g., information obtained from crystal structures and/or molecular modeling) is used to assess the likelihood that a given amino acid residue in a variable region is (a) involved in antigen binding, (b) exposed on the antibody surface (i.e., accessible to solvent), or (c) buried within the antibody variable region (i.e., involved in maintaining the structure of the variable region). Furthermore, in certain embodiments, human variable region consensus sequences are generated to identify residues that are conserved among human variable regions. In certain embodiments, that information provides guidance as to whether an amino acid residue in the variable region of a non-human antibody should be substituted.

4.3.2. Antibody Isotypes

In certain embodiments, an antibody against GHP1 is of any isotype selected from IgM, IgD, IgG, IgA, and IgE. In certain embodiments, an antibody against GHP1 is of the IgG isotype. In certain such embodiments, an antibody is of the subclass IgG1, IgG2, IgG3, or IgG4. In certain embodiments, an antibody against GHP1 is of the IgM isotype. In certain is such embodiments, an antibody is of the subclass IgM1 or IgM2. In certain embodiments, an antibody against GHP1 is of the IgA isotype. In certain such embodiments, an antibody is of the subclass IgA1 or IgA2. In certain embodiments, an antibody against GHP1 comprises a human kappa light chain and a human IgG1 or IgG2 heavy chain. In certain embodiments, an antibody against GHP1 comprises a mouse kappa light chain and a mouse IgG1 or IgG2 heavy chain.

4.3.3. Modified Antibodies

In various embodiments, an antibody is modified to alter one or more of its properties. In certain embodiments, a modified antibody may possess advantages over an unmodified antibody, such as increased stability, increased time in circulation, or decreased immunogenicity (see, e.g., U.S. Pat. No. 4,179,337). In certain embodiments, an antibody is modified by linking it to a nonproteinaceous moiety. In certain embodiments, an antibody is modified by altering the glycosylation state of the antibody, e.g., by altering the number, type, linkage, and/or position of carbohydrate chains on the antibody. In certain embodiments, an antibody is altered so that it is not glycosylated.

In certain embodiments, one or more chemical moieties are linked to the amino acid backbone and/or carbohydrate residues of the antibody. Certain exemplary methods for linking a chemical moiety to an antibody are known to those skilled in the art. Such methods include, but are not limited to, acylation reactions or alkylation reactions. See, for example, EP 0 401 384; Malik et al. (1992), Exp. Hematol., 20:1028-1035; Francis (1992), Focus on Growth Factors, 3(2):4-10, published by Mediscript, Mountain Court, Friern Barnet Lane, London N20 OLD, UK; EP 0 154 316; EP 0 401 384; WO 92/16221; WO 95/34326; WO 95/13312; WO 96/11953; WO 96/19459 and WO 96/19459. In certain embodiments, any of these reactions are used to generate an antibody that is chemically modified at its amino-terminus.

In certain embodiments, an antibody is linked to a detectable label, such as an enzymatic, fluorescent, isotopic or affinity label. In certain such embodiments, a detectable label allows for the detection or isolation of the antibody. In certain embodiments, a detectable label allows for the detection of an antigen bound by the antibody.

In certain embodiments, an antibody is modified by linking it to one or more polymers. In certain embodiments, an antibody is linked to one or more water-soluble polymers. In certain such embodiments, linkage to a water-soluble polymer reduces the likelihood that the antibody will precipitate in an aqueous environment, such as a physiological environment. In certain embodiments, a therapeutic antibody is linked to a water-soluble polymer.

In certain embodiments, one skilled in the art can select a suitable water-soluble polymer based on considerations including, but not limited to, whether the polymer/antibody conjugate will be used in the treatment of a patient and, if so, the pharmacological profile of the antibody (e.g., half-life, dosage, activity, antigenicity, and/or other factors).

Certain exemplary clinically acceptable, water-soluble polymers include, but are not limited to, polyethylene glycol (PEG); polyethylene glycol propionaldehyde; copolymers of ethylene glycol/propylene glycol; monomethoxy-polyethylene glycol; carboxymethylcellulose; dextran; polyvinyl alcohol (PVA); polyvinyl pyrrolidone, poly-1,3-dioxolane; poly-1,3,6-trioxane; ethylene/maleic anhydride copolymer; poly-β-amino acids (either homopolymers or random copolymers); poly(n-vinyl pyrrolidone)polyethylene glycol; polypropylene glycol homopolymers (PPG) and other polyalkylene oxides; polypropylene oxide/ethylene oxide copolymers; polyoxyethylated polyols (POG) (e.g., glycerol) and other polyoxyethylated polyols; polyoxyethylated sorbitol, polyoxyethylated glucose, colonic acids or other carbohydrate polymers; and Ficoll, dextran, or mixtures thereof. Certain exemplary PEGs include, but are not limited to, certain forms known in the art to be useful in antibody modification, such as mono-($C_1$-$C_{10}$) alkoxy- or aryloxy-PEG. In certain embodiments, PEG propionaldehyde may have advantages in manufacturing due to its stability in water.

In certain embodiments, a water-soluble polymer is of any molecular weight. In certain embodiments, a water-soluble polymer is branched or unbranched. In certain embodiments, a water-soluble polymer has an average molecular weight of about 2 kDa to about 100 kDa, including all points between the end points of the range. In certain embodiments, a water-soluble polymer has an average molecular weight of about 5 kDa to about 40 kDa. In certain embodiments, a water-soluble polymer has an average molecular weight of about 10 kDa to about 35 kDa. In certain embodiments, a water-soluble polymer has an average molecular weight of about 15 kDa to about 30 kDa.

In certain embodiments, an antibody is linked to PEG (i.e., an antibody is "pegylated"). In various embodiments, PEG has low toxicity in mammals. See Carpenter et al. (1971) Toxicol. Appl. Pharmacol., 18:35-40. Notably, a PEG adduct of adenosine deaminase was approved in the United States for use in humans for the treatment of severe combined immunodeficiency syndrome. In various embodiments, PEG may reduce the immunogenicity of antibodies. For example, in certain embodiments, linkage of PEG to an antibody having non-human sequences may reduce the antigenicity of that antibody when administered to a human.

In certain embodiments, a polymer is linked to one or more reactive amino acid residues in an antibody. Certain exemplary reactive amino acid residues include, but are not limited to, the alpha-amino group of the amino-terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, and activated glycosyl chains linked to certain asparagine, serine or threonine residues. Certain exemplary activated forms of PEG ("PEG reagents") suitable for direct reaction with proteins are known to those skilled in the art. For example, in certain embodiments, PEG reagents suitable for linkage to amino groups include, but are not limited to, active esters of carboxylic acid or carbonate derivatives of PEG, for example, those in which the leaving groups are N-hydroxysuccinimide, p-nitrophenol, imidazole or 1-hydroxy-2-nitrobenzene-4-sulfonate. In certain embodiments, PEG reagents containing maleimido or haloacetyl groups are used to modify sulfhydryl groups. In certain embodiments, PEG reagents containing amino, hydrazine and/or hydrazide groups may be used in reactions with aldehydes generated by periodate oxidation of carbohydrate groups in proteins.

In certain embodiments, a water-soluble polymer has at least one reactive hydroxy group. In certain embodiments, an activated derivative of a water-soluble polymer, such as PEG, is created by reacting the water-soluble polymer with an activating group. In certain embodiments, an activating group may be monofunctional, bifunctional, or multifunctional. Certain exemplary activating groups that can be used to link a water-soluble polymer to two or more antibodies include, but are not limited to, the following groups: sulfone (e.g., chlorosulfone, vinylsulfone and divinylsulfone), maleimide, sulfhydryl, thiol, triflate, tresylate, azidirine, oxirane and 5-pyridyl. In certain embodiments, a PEG derivative is typically stable against hydrolysis for extended periods in aqueous environments at pHs of about 11 or less. In certain embodiments, a PEG derivative linked to another molecule, such as an antibody, confers stability from hydrolysis on that molecule. Certain exemplary homobifunctional PEG derivatives include, but are not limited to, PEG-bis-chlorosulfone and PEG-bis-vinylsulfone (see WO 95/13312).

4.4. CERTAIN METHODS OF MAKING MONOCLONAL ANTIBODIES

4.4.1. Certain Hybridoma Methods

In certain embodiments, monoclonal antibodies are produced by standard techniques. In certain embodiments, monoclonal antibodies are produced by hybridoma-based methods. Certain such methods are known to those skilled in the art. See, e.g., Kohler et al. (1975) Nature 256:495-497; Harlow and Lane (1988) Antibodies: A Laboratory Manual Ch. 6 (Cold Spring Harbor Laboratory, Cold Spring Harbor, N.Y.). In certain such embodiments, a suitable animal, such as a mouse, rat, hamster, monkey, or other mammal, is immunized with an immunogen to produce antibody-secreting cells. In certain embodiments, the antibody-secreting cells are B-cells, such as lymphocytes or splenocytes. In certain embodiments, lymphocytes (e.g., human lymphocytes) are immunized in vitro to generate antibody-secreting cells. See, e.g., Borreback et al. (1988) Proc. Nat'l Acad. Sci. USA 85:3995-3999.

In certain embodiments, antibody secreting cells are fused with an "immortalized" cell line, such as a myeloid-type cell line, to produce hybridoma cells. In certain embodiments, hybridoma cells that produce the desired antibodies are identified, for example, by ELISA. In certain embodiments, such cells can then be subcloned and cultured using standard methods. In certain embodiments, such cells can also be grown in vivo as ascites tumors in a suitable animal host. In certain embodiments, monoclonal antibodies are isolated from hybridoma culture medium, serum, or ascites fluid using standard separation procedures, such as affinity chromatography. Guidance for the production of hybridomas and the purification of monoclonal antibodies according to certain embodiments is provided, for example, in Harlow and Lane (1988) Antibodies: A Laboratory Manual Ch. 8 (Cold Spring Harbor Laboratory, Cold Spring Harbor, N.Y.).

In certain embodiments, mouse monoclonal antibodies are produced by immunizing genetically altered mice with an immunogen. In certain such embodiments, the mice are GHP1-deficient mice, that partially or completely lack GHP1 function. In certain such embodiments, the mice are "knockout" mice that functionally lack all or part of a gene encoding GHP1 (i.e., mice incorporating a functionally "null" allele). In certain embodiments, such knockout mice are immunized with mouse GHP1. In certain such embodiments, such knockout mice are immunized with human GHP1.

In certain embodiments, human monoclonal antibodies are raised in transgenic animals (e.g., mice) that are capable of producing human antibodies. See, e.g., U.S. Pat. Nos. 6,075,181 A and 6,114,598 A; and WO 98/24893 A2. For example, in certain embodiments, human immunoglobulin genes are introduced (e.g., using yeast artificial chromosomes, human chromosome fragments, or germline integration) into mice in which the endogenous Ig genes have been inactivated. See, e.g., Jakobovits et al. (1993) Nature 362:255-258; Tomizuka et al. (2000) Proc. Nat'l Acad. Sci. USA 97:722-727; and Mendez et al. (1997) Nat. Genet. 15:146-156 (describing the XenoMouse II® line of transgenic mice).

In certain embodiments, such transgenic mice are immunized with an immunogen. In certain such embodiments, lymphatic cells (such as B-cells) from mice that express antibodies are obtained. In certain such embodiments, such recovered cells are fused with an "immortalized" cell line, such as a myeloid-type cell line, to produce hybridoma cells. In certain such embodiments, hybridoma cells are screened and selected to identify those that produce antibodies specific to the antigen of interest. Certain exemplary methods and transgenic mice suitable for the production of human monoclonal antibodies are described, e.g., in Jakobovits et al. (1993) Nature 362:255-258; Jakobovits (1995) Curr. Opin. Biotechnol. 6:561-566; Lonberg et al. (1995) Int. Rev. Immunol. 13:65-93; Fishwild et al. (1996) Nat. Biotechnol. 14:845-851; Mendez et al. (1997) Nat. Genet. 15:146-156; Green (1999) J. Immunol. Methods 231:11-23; Tomizuka et al. (2000) Proc. Nat'l Acad. Sci. USA 97:722-727; and reviewed in Little et al. (2000) Immunol. Today 21:364-370; and WO 98/24893.

4.4.2. Certain Display-Based Methods

In certain embodiments, human monoclonal antibodies are produced using a display-based method, such as, for example, any of those described below.

In certain embodiments, a monoclonal antibody is produced using phage display techniques. Certain exemplary antibody phage display methods are known to those skilled in the art and are described, for example, in Hoogenboom, Overview of Antibody Phage-Display Technology and Its Applications, from Methods in Molecular Biology: Antibody Phage Display Methods and Protocols (2002) 178:1-37 (O'Brien and Aitken, eds., Human Press, Totowa, N.J.). For example, in certain embodiments, a library of antibodies are displayed on the surface of a filamentous phage, such as the nonlytic filamentous phage fd or M13. In certain embodiments, the antibodies are antibody fragments, such as scFvs, Fabs, Fvs with an engineered intermolecular disulfide bond to stabilize the VH-VL pair, and diabodies. In certain embodiments, antibodies with the desired binding specificity can then be selected. Certain exemplary embodiments of antibody phage display methods are described in further detail below.

In certain embodiments, an antibody phage-display library can be prepared using certain methods known to those skilled in the art. See, e.g., Hoogenboom, Overview of Antibody Phage-Display Technology and Its Applications, from Methods in Molecular Biology: Antibody Phage Display: Methods and Protocols (2002) 178:1-37 (O'Brien and Aitken, eds., Human Press, Totowa, N.J.). In certain embodiments, variable gene repertoires are prepared by PCR amplification of genomic DNA or cDNA derived from the mRNA of antibody-secreting cells. For example, in certain embodiments, cDNA is prepared from mRNA of B-cells. In certain embodiments, cDNA encoding the variable regions of heavy and light chains is amplified, for example, by PCR.

In certain embodiments, heavy chain cDNA and light chain cDNA are cloned into a suitable vector. In certain embodiments, heavy chain cDNA and light chain cDNA are randomly combined during the cloning process, thereby resulting in the assembly of a cDNA library encoding diverse scFvs or Fabs. In certain embodiments, heavy chain cDNA and light chain cDNA are ligated before being cloned into a suitable vector. In certain embodiments, heavy chain cDNA and light chain cDNA are ligated by stepwise cloning into a suitable vector.

In certain embodiments, cDNA is cloned into a phage display vector, such as a phagemid vector. Certain exemplary phagemid vectors, such as pCES1, are known to those skilled in the art. In certain embodiments, cDNA encoding both heavy and light chains is present on the same vector. For example, in certain embodiments, cDNA encoding scFvs are cloned in frame with all or a portion of gene III, which encodes the minor phage coat protein pIII. In certain such embodiments, the phagemid directs the expression of the scFv-pIII fusion on the phage surface. Alternatively, in certain embodiments, cDNA encoding heavy chain (or light chain) is cloned in frame with all or a portion of gene III, and cDNA encoding light chain (or heavy chain) is cloned downstream of a signal sequence in the same vector. The signal sequence directs expression of the light chain (or heavy chain) into the periplasm of the host cell, where the heavy and light chains assemble into Fab fragments.

Alternatively, in certain embodiments, cDNA encoding heavy chain and cDNA encoding light chain are present on separate vectors. In certain such embodiments, heavy chain and light chain cDNA is cloned separately, one into a phagemid and the other into a phage vector, which both contain signals for in vivo recombination in the host cell.

In certain embodiments, recombinant phagemid or phage vectors are introduced into a suitable bacterial host, such as *E. coli*. In certain embodiments using phagemid, the host is infected with helper phage to supply phage structural proteins, thereby allowing expression of phage particles carrying the antibody-pIII fusion protein on the phage surface.

In certain embodiments, "synthetic" antibody libraries are constructed using repertoires of variable genes that are rearranged in vitro. For example, in certain embodiments, individual gene segments encoding heavy or light chains (V-D-J or V-J, respectively) are randomly combined using PCR. In certain such embodiments, additional sequence diversity can be introduced into the CDRs, and possibly FRs, e.g., by error prone PCR. In certain such embodiments, additional sequence diversity is introduced into CDR3, e.g., H3 of the heavy chain.

In certain embodiments, "naïve" or "universal" phage display libraries are constructed as described above using nucleic acid from an unimmunized animal. In certain embodiments, the unimmunized animal is a human. In certain embodiments, "immunized" phage display libraries are constructed as described above using nucleic acid from an immunized animal. In certain embodiments, the immunized animal is a human, rat, mouse, hamster, or monkey. In certain such embodiments, the animals are immunized with any of the immunogens described below.

Certain exemplary universal human antibody phage display libraries are available from commercial sources. Certain exemplary libraries include, but are not limited to, the HuCAL® series of libraries from MorphoSys AG (Martinstreid/Munich, Germany); libraries from Crucell (Leiden, the Netherlands) using MAbstracte technology; the n-CoDeR™ Fab library from BioInvent (Lund, Sweden); and libraries available from Cambridge Antibody Technology (Cambridge, UK).

In certain embodiments, the selection of antibodies having the desired binding specificity from a phage display library is achieved by successive panning steps. In certain embodiments of panning, library phage preparations are exposed to antigen. In certain such embodiments, the phage-antigen complexes are washed, and unbound phage are discarded. In certain such embodiments, bound phage are recovered and subsequently amplified by infecting *E. coli*. In certain such embodiments, monoclonal antibody-producing phage may be cloned by picking single plaques. In certain embodiments, the above process is repeated.

In certain embodiments, the antigen used in panning is any of the immunogens described below. In certain embodiments, the antigen is immobilized on a solid support to allow purification of antigen-binding phage by affinity chromatography.

In certain embodiments, the antigen is biotinylated, thereby allowing the separation of bound phage from unbound phage using streptavidin-coated magnetic beads.

In certain embodiments, the antigen may be immobilized on cells (for direct panning), in tissue cryosections, or on membranes (e.g., nylon or nitrocellulose membranes). Other variations of certain panning procedures may be routinely determined by one skilled in the art.

In certain embodiments, a yeast display system is used to produce monoclonal antibodies. In certain such systems, an antibody is expressed as a fusion protein with all or a portion of the yeast AGA2 protein, which becomes displayed on the surface of the yeast cell wall. In certain such embodiments, yeast cells expressing antibodies with the desired binding specificity can then be identified by exposing the cells to fluorescently labeled antigen. In certain such embodiments, yeast cells that bind the antigen can then be isolated by flow cytometry. See, e.g., Boder et al. (1997) Nat. Biotechnol. 15:553-557.

4.4.3. Certain Affinity Maturation Methods

In certain embodiments, the affinity of an antibody for a particular antigen is increased by subjecting the antibody to affinity maturation (or "directed evolution") in vitro. In vivo, native antibodies undergo affinity maturation through somatic hypermutation followed by selection. Certain in vitro methods mimic that in vivo process, thereby allowing the production of antibodies having affinities that equal or surpass that of native antibodies.

In certain embodiments of affinity maturation, mutations are introduced into a nucleic acid sequence encoding the variable region of an antibody having the desired binding specificity. See, e.g., Hudson et al. (2003) Nature Med. 9:129-134; Brekke et al. (2002) Nature Reviews 2:52-62. In certain embodiments, mutations are introduced into the variable region of the heavy chain, light chain, or both. In certain embodiments, mutations are introduced into one or more CDRS. In certain such embodiments, mutations are introduced into H3, L3, or both. In certain embodiments, mutations are introduced into one or more FRs. In certain embodiments, a library of mutations is created, for example, in a phage, ribosome, or yeast display library, so that antibodies with increased affinity may be identified by standard screening methods. See, e.g., Boder et al. (2000) Proc. Nat'l Acad. Sci. USA 97:10701-10705; Foote et al. (2000) Proc. Nat'l Acad. Sci. USA 97:10679-10681; Hoogenboom, Overview of Antibody Phage-Display Technology and Its Applications, from Methods in Molecular Biology: Antibody Phage Display: Methods and Protocols (2002) 178:1-37 (O'Brien and Aitken, eds., Human Press, Totowa, N.J.); and Hanes et al. (1998) Proc. Nat'l Acad. Sci. USA 95:14130-14135.

In certain embodiments, mutations are introduced by site-specific mutagenesis based on information on the antibody's structure, e.g., the antigen binding site. In certain embodiments, mutations are introduced using combinatorial mutagenesis of CDRs. In certain embodiments, all or a portion of the variable region coding sequence is randomly mutagenized, e.g., using E. coli mutator cells, homologous gene rearrangement, or error prone PCR. In certain embodiments, mutations are introduced using "DNA shuffling." See, e.g., Crameri et al. (1996) Nature Med. 2:100-102; Fermer et al. (2004) Tumor Biology 25:7-13.

In certain embodiments, "chain shuffling" is used to generate antibodies with increased affinity. In certain embodiments of chain shuffling, one of the chains, e.g., the light chain, is replaced with a repertoire of light chains, while the other chain, e.g., the heavy chain, is unchanged, thus providing specificity. In certain such embodiments, a library of chain shuffled antibodies is created, wherein the unchanged heavy chain is expressed in combination with each light chain from the repertoire of light chains. In certain embodiments, such libraries may then be screened for antibodies with increased affinity. In certain embodiments, both the heavy and light chains are sequentially replaced. In certain embodiments, only the variable regions of the heavy and/or light chains are replaced. In certain embodiments, only a portion of the variable regions, e.g., CDRs, of the heavy and/or light chains are replaced. See, e.g., Hudson et al. (2003) Nature Med. 9:129-134; Brekke et al. (2002) Nature Reviews 2:52-62; Kang et al. (1991) Proc. Nat'l Acad. Sci. USA 88:11120-11123; Marks et al. (1992) Biotechnology 10:779-83.

In certain embodiments, mouse monoclonal antibodies that selectively bind human GHP1 (including, but not limited to, mouse monoclonal antibodies raised against mouse GHP1 but which specifically bind (i.e., cross react) with human GHP1) are subject to sequential chain shuffling. In certain embodiments, for example, the heavy chain of a given mouse monoclonal antibody is combined with a new repertoire of human light chains, and antibodies with the desired affinity are selected. In certain such embodiments, the light chains of the selected antibodies are then combined with a new repertoire of human heavy chains, and antibodies with the desired affinity are selected. Thus, in certain embodiments, human antibodies having the desired antigen binding specificity and affinity are selected.

Alternatively, in certain embodiments, the heavy chain of a given mouse monoclonal antibody is combined with a new repertoire of human light chains, and antibodies with the desired affinity are selected from this first round of shuffling. In certain embodiments, the light chain of the original mouse monoclonal antibody is combined with a new repertoire of human heavy chains, and antibodies with the desired affinity are selected from this second round of shuffling. In certain embodiments, human light-chains from the antibodies selected in the first round of shuffling are then combined with human heavy chains from the antibodies selected in the second round of shuffling. Thus, in certain embodiments, human antibodies having the desired antigen binding specificity and affinity are selected.

In certain embodiments, a "ribosome display" method is used that alternates antibody selection with affinity maturation. In certain embodiments of a ribosome display method, antibody-encoding nucleic acid is amplified by RT-PCR between the selection steps. Thus, in certain embodiments, error prone polymerases may be used to introduce mutations into the nucleic acid. A nonlimiting example of such a method is described in detail in Hanes et al. (1998) Proc. Nat'l Acad. Sci. USA 95:14130-14135.

4.4.4. Certain Recombinant Methods

In certain embodiments, a monoclonal antibody is produced by recombinant techniques. See, e.g., U.S. Pat. No. 4,816,567. In certain such embodiments, nucleic acid encoding monoclonal antibody chains are cloned and expressed in a suitable host cell. For example, in certain embodiments, RNA can be prepared from cells expressing the desired antibody, such as mature B-cells or hybridoma cells, using standard methods. In certain embodiments, the RNA can then be used to make cDNA using standard methods. In certain embodiments, cDNA encoding a heavy or light chain polypeptide is amplified, for example, by PCR, using specific oligonucleotide primers. In certain embodiments, the cDNA is cloned into a suitable expression vector. In certain embodiments, the expression vector is then transformed or transfected into a suitable host cell, such as a host cell that does not endogenously produce antibody. Certain exemplary host cells include, but are not limited to, *E. coli*, COS cells, Chinese hamster ovary (CHO) cells, and myeloma cells. In certain embodiments, wherein heavy and light chains are coexpressed in the same host, reconstituted antibody may be isolated.

In certain embodiments, cDNA encoding a heavy or light chain can be modified. For example, in certain embodiments, the constant region of a mouse heavy or light chain can be replaced with the constant region of a human heavy or light chain. In this manner, in certain embodiments, a chimeric antibody can be produced which possesses human antibody constant regions but retains the binding specificity of a mouse antibody.

In certain embodiments, recombinant antibodies can be expressed in certain cell lines. In certain embodiments, sequences encoding particular antibodies can be used for transformation of a suitable mammalian host cell. According to certain embodiments, transformation can be by any known method for introducing polynucleotides into a host cell.

Certain exemplary methods include, but are not limited to, packaging the polynucleotide in a virus (or into a viral, vector) and transducing a host cell with the virus (or vector) and using certain transfection procedures known in the art, as exemplified by U.S. Pat. Nos. 4,399,216, 4,912,040, 4,740,461, and 4,959,455. In certain embodiments, the transformation procedure used may depend upon the host to be transformed. Certain exemplary methods for introduction of heterologous polynucleotides into mammalian cells are known in the art and include, but are not limited to, dextran-mediated transfection, calcium phosphate precipitation, polybrene mediated transfection, protoplast fusion, electroporation, encapsulation of the polynucleotide(s) in liposomes, and direct microinjection of the DNA into nuclei.

Certain exemplary mammalian cell lines available as hosts for expression are known in the art and include, but are not limited to, many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, is cell lines may be selected by determining which cell lines produce high levels of antibodies that specifically bind GHP1.

4.5. Certain Polypeptide Immunogens

In certain embodiments, to generate antibodies, an animal is immunized with an immunogen. In certain embodiments, an immunogen is a polypeptide comprising GHP1. In certain embodiments, an immunogen comprises a human GHP1. In certain embodiments, an immunogen is a polypeptide comprising a fragment of GHP1. In certain such embodiments, a peptide is selected that is likely to be immunogenic. In certain such embodiments, a peptide is selected that is predicted to be hydrophilic and/or likely to be exposed on the surface of native GHP1 in its folded state. Exemplary guidance for selecting suitable immunogenic peptides is provided, for example, in Ausubel et al. (1989) Current Protocols in Molecular Biology Ch. 11.14 (John Wiley & Sons, NY); and Harlow and Lane (1988) Antibodies: A Laboratory Manual Ch. 5 (Cold Spring Harbor Laboratory, Cold Spring Harbor, N.Y.).

Certain exemplary algorithms are known to those skilled in the art for predicting whether a peptide segment of a protein is hydrophilic and therefore likely to be exposed on the surface of the protein. Certain such algorithms use the primary sequence information of a protein to make such predictions. Certain such algorithms are based on the method of, for example, Hopp and Woods (1981) Proc. Nat'l Acad. Sci. USA 78:3824-3828, or Kyte and Doolittle (1982) J. Mol. Biol. 157:105-132. Certain exemplary algorithms are known to those skilled in the art for predicting the secondary structure of a protein based on the primary amino acid sequence of the protein. See, e.g., Corrigan et al. (1982) Comput. Programs Biomed. 3:163-168. Certain such algorithms are based on the method of, for example, Chou and Fasman (1978) Ann. Rev. Biochem. 47:25-276. In certain embodiments, peptide segments that are predicted to form β-turns, and are therefore likely to be exposed on the surface of a protein, may be selected as immunogens.

In certain embodiments, an animal is immunized with an immunogen and one or more adjuvants. In certain embodiments, an adjuvant is used to increase the immunological response, depending on the host species. Certain exemplary adjuvants include, but are not limited to, Freund's adjuvant (complete and incomplete), mineral salts such as aluminum hydroxide or aluminum phosphate, surface active substances, chitosan, lysolecithin, pluronic polyols, polyanions, peptides, oil emulsions, and potentially useful human adjuvants such as BCG (bacille Calmette-Guerin) and *Corynebacterium parvum*. In certain embodiments, the immune response to an immunogen, e.g., a peptide immunogen, is enhanced by coupling the immunogen to another immunogenic molecule or "carrier protein." Certain exemplary carrier proteins include, but are not limited to, keyhole limpet hemocyanin (KLH), tetanus toxoid, diphtheria toxoid, ovalbumin, cholera toxoid, and immunogenic fragments thereof. For exemplary guidance in coupling peptide immunogens to carrier proteins, see, e.g., Ausubel et al. (1989) Current Protocols in Molecular Biology Ch. 11.15 (John Wiley & Sons, NY); and Harlow and Lane (1988) Antibodies: A Laboratory Manual Ch. 5 (Cold Spring Harbor Laboratory, Cold Spring Harbor, N.Y.).

In certain embodiments, any of the above immunogens can be produced using standard recombinant methods. For example, in certain embodiments, a polynucleotide encoding a mouse or human GHP1 or a fragment of that polynucleotide may be cloned into a suitable expression vector. For certain exemplary methods of recombinant protein expression, see, e.g., Ausubel et al. (1991) Current Protocols in Molecular Biology Ch. 16 (John Wiley & Sons, NY).

4.6. CERTAIN ASSAYS

4.6.1. Certain Binding Assays

In certain embodiments, antibodies are screened for binding to GHP1 using certain routine methods that detect binding of antibody to antigen. For example, in certain embodiments, the ability of a monoclonal antibody to bind GHP1 is assayed by standard immunoblotting methods, such as Western blot. See, e.g., Ausubel et al. (1992) Current Protocols in Molecular Biology Ch. 10.8 (John Wiley & Sons, NY); Harlow and Lane (1988) Antibodies: A Laboratory Manual (Cold Spring Harbor Laboratory, Cold Spring Harbor, N.Y.). In certain embodiments, GHP1 to be used in such assays may be isolated or may be present in a complex mixture of proteins and/or macromolecules.

In certain embodiments, the ability of a monoclonal antibody to bind GHP1 is assayed using a competitive binding assay, which evaluates the ability of a candidate antibody to compete with a known GHP1 ligand. In certain embodiments, a competitive binding assay is performed using ELISA. See, e.g., Harlow and Lane (1988) Antibodies: A Laboratory Manual Ch. 14 (Cold Spring Harbor Laboratory, Cold Spring Harbor, N.Y.).

In certain embodiments, a binding assay is used to quantify the binding kinetics (e.g., rate constant) or the binding affinity (e.g., association or dissociation constant) of an antibody against GHP1. In certain embodiments, the kinetics or affinity of binding is determined in the "solid-phase" by immobilizing antigen (e.g., GHP1) on a solid support. The immobilized antigen "captures" antibody from solution. In certain embodiments, binding kinetics or binding affinity is determined using ELISA-based methods. In certain embodiments, binding kinetics or binding affinity is determined using biosensor-based technology, such as Biacore surface plasmon resonance technology (Biacore, Piscataway, N.J.). Certain such methods are known to those skilled in the art. See, e.g., McCafferty et al. (eds.) (1996) Antibody Engineering: A Practical Approach (IRL, Oxford, UK); Goldberg et al. (1993) Curr. Opin. Immunol. 5:278-281; Karlsson et al. (1991) J. Immunol. Methods 145:229-240; Malmqvist (1993) Curr. Opin. Immunol. 5:282-286; for review, see Hoogenboom, Overview of Antibody Phage-Display Technology and Its Applications, from Methods in Molecular Biology: Antibody Phage Display Methods and Protocols (2002) 178:1-37 at 19 (O'Brien and Aitken, eds., Human Press, Totowa, N.J.).

In certain embodiments, the binding kinetics or binding affinity of a Fab fragment that specifically binds to GHP1 is determined. In certain instances, Fab fragments have the property of not multimerizing. Multimerization can, in certain instances, complicate the measurement of binding kinetics and binding affinity in "solid phase" methods. See, e.g., Hoogenboom, Overview of Antibody Phage-Display Technology and Its Applications, from Methods in Molecular Biology: Antibody Phage Display: Methods and Protocols (2002) 178:1-37 at 19 (O'Brien and Aitken, eds., Human Press, Totowa, N.J.). Thus, in certain embodiments, a Fab fragment that specifically binds to GHP1 is suitable for use in a binding assay in which antigen is immobilized to a solid support, such as, for example, an ELISA-based assay or a Biacore assay. In certain embodiments, Fab fragments are generated from an intact antibody that specifically binds to GHP1 using enzymatic methods. In certain embodiments, Fab fragments are produced by expressing nucleic acids encoding Fab fragments in a recombinant expression system, such as those described above, Part V.D.3.

In certain embodiments, the binding kinetics or binding affinity of an antibody against GHP1 is determined using "solution phase" methods. In such methods, the kinetics or affinity of binding is measured for an antibody-antigen complex in solution. Certain such methods are known to those skilled in the art. A nonlimiting example of such a method is the "kinetic exclusion assay," or "KinExA." See, e.g., Blake et al. (1996) J. Biol. Chem. 271:27677-27685; Drake et al. (2004) Anal. Biochem. 328:35-43 (comparing Biacore "solid phase" and KinExA "solution phase" methods). In certain embodiments, instrumentation for performing KinExA is supplied by Sapidyne Instruments, Inc. (Boise, Id.).

In certain embodiments, the binding kinetics or binding affinity of a multivalent antibody or an antibody that multimerizes is determined using a solution phase method. In certain instances, the measurement of the binding kinetics or the binding affinity of a multivalent antibody or an antibody that multimerizes is amenable to solution phase analysis.

In certain embodiments, the binding affinity of an anti-GHP1 antibody is about $10^{-6}$ M or less. In certain embodiments, the binding affinity of an anti-GHP1 antibody is about $10^{-7}$ M, about $10^{-8}$ M, or about $10^{-9}$ M or less. See, e.g., Hudson et al. (2003) Nature Med. 9:129-134. In certain embodiments, binding affinities of less than $10^{-9}$ M (e.g., binding affinities from about 500 µM to about 0.5 µM) are achievable, e.g., using affinity maturation techniques. See, e.g., Boder et al. (2000) Proc. Nat'l Acad. Sci. USA 97:10701-10705.

In certain embodiments, a monoclonal antibody that was raised against mouse GHP1 is screened for specific binding to human GHP1 using certain routine detection methods, e.g., such as those described herein. The ability of a monoclonal antibody to bind both mouse and human GHP1 (i.e., to demonstrate "cross-reactivity") indicates the presence of the same therapeutically exploitable epitope in mouse and human GHP1. In certain embodiments of detection methods that use denaturing conditions (e.g., Western blot), cross-reactivity indicates that a mouse monoclonal antibody binds to the same "linear" epitope in mouse and human GHP1. In certain embodiments of detection methods that use non-denaturing conditions, cross-reactivity indicates that a mouse monoclonal antibody binds to the same epitope (e.g., a linear epitope or a conformational epitope) in mouse and human GHP1.

4.6.2. Certain Methods for Epitope Mapping

In various embodiments, the epitope to which a monoclonal antibody binds is identified by any of a number of assays. Certain exemplary assays are described, for example, in Morris, Methods in Molecular Biology Vol. 66: Epitope Mapping Protocols (1996) (Humana Press, Totowa, N.J.). For example, epitope mapping may be achieved by gene fragment expression assays or peptide-based assays. In certain embodiments of a gene fragment expression assay, for example, nucleic acids encoding fragments of GHP1 are expressed in prokaryotic cells and isolated. In certain such embodiments, the ability of a monoclonal antibody to bind those fragments is then assessed, e.g., by immunoprecipitation or immunoblotting. In certain embodiments, nucleic acids encoding fragments of GHP1 are transcribed and translated in vitro in the presence of radioactive amino acids. The radioactively labeled fragments of GHP1 are then tested for binding to a monoclonal antibody. In certain embodiments, fragments of GHP1 are generated by proteolytic fragmentation. In certain embodiments, an epitope is identified using libraries of random peptides displayed on the surface of phage or yeast. In certain embodiments, an epitope is identified by testing a library of overlapping synthetic peptide fragments of GHP1 for binding to a monoclonal antibody. In certain embodiments, an epitope is identified using a competition assay, such as those described below.

4.6.3. Certain Assays for Identifying Antibody Agonists

In certain embodiments, monoclonal antibodies are screened for antibodies that stabilize or enhance GHP1 binding, i.e., those that increase an activity of GHP1 in vivo and/or in vitro.

4.7. GHP1 TRANSGENIC ANIMALS AND KNOCKOUT ANIMALS

Certain embodiments of the described invention relate to the engineering and isolation of totipotent cells that incorporate a mutated GHP1 allele. When such totipotent cells are embryonic stem (ES) cells, the mutated ES cells can be introduced into embryos to generate animals capable of germline transmission of the mutated allele. Where the ES cells are mouse ES cells, the resulting animals capable of germline transmission of mutated GHP1 alleles can be generated and maintained as outbred or inbred mouse lines. Mice capable of germline transmission of a mutated GHP1 allele are described below.

In certain embodiments, cells genetically engineered to be deficient in GHP1 production can be used to produce animals capable of germline transmission of the mutated GHP1 allele. When such animals are bred to produce animals homozygous for the mutated allele, the animals manifest a phenotype of significantly elevated lipid levels. Accordingly, the described GHP1 knockout animals are useful as models for GHP1-related disorders, and in the testing of potency GHP1 preparations for reducing blood lipid levels. The described animals are also useful in assessing the in vivo characteristics of GHP1 preparations, and the functional identification of engineered versions of GHP1. In certain additional embodiments, the counterpart animals of the described GHP1-deficient animals include animals that express enhanced levels of GHP1 activity (which should not prove to have lower blood lipid levels). Accordingly, certain embodiments of the invention provide for the production and use of transgenic animals that carry a GHP1 transgene in essentially all of their cells, as well as transgenic animals that carry a GHP1 transgene in some, but not all their cells, i.e., mosaic animals or somatic cell transgenics. Animals of any species, including, but not limited to, mice, rats, rabbits, guinea pigs, pigs, micro-pigs, goats, and non-human primates, e.g., baboons, monkeys, and chimpanzees, can be used to generate transgenic animals carrying recombinant polynucleotides encoding a GHP1 product. GHP1 transgenes can be integrated as a single transgene or in concatamers, e.g., head-to-head tandems or head-to-tail tandems. The transgene can also be selectively introduced into and activated in a particular cell-type by following, for example, the teaching of Lakso et al., 1992, Proc. Natl. Acad. Sci. USA 89:6232-6236. Although the endogenous expression of GHP1 is widespread, the regulatory sequences required for such a cell-type specific activation will depend upon the particular cell-type of interest, and will be apparent to those of skill in the art.

When it is desired that the GHP1 transgene be integrated into the chromosomal site of the endogenous copy of the GHP1 gene, gene targeting is preferred. Briefly, when such a technique is to be utilized, vectors containing some nucleotide sequences homologous to the endogenous GHP1 gene are designed for the purpose of integrating, via homologous recombination with chromosomal sequences, into and disrupting the function of the nucleotide sequence of the endogenous GHP1 gene and inserting the transgene (i.e., to produce a "knockin" allele). In a similar fashion, the expression of the endogenous GHP1 gene can also be eliminated by inserting non-functional sequences into the endogenous GHP1 gene. The transgene can also be selectively introduced into a particular cell-type, thus inactivating the endogenous GHP1 gene in only that cell-type, by following, for example, the teaching of Gu et al., 1994, Science 265:103-106. The regulatory sequences required for such a cell-type specific inactivation will depend upon the particular cell-type of interest.

Any technique known in the art can be used to introduce a GHP1 transgene into animals to produce the founder lines of transgenic animals. Such techniques include, but ate not limited to, pronuclear microinjection (U.S. Pat. No. 4,873,191, incorporated herein by reference); retrovirus-mediated gene transfer into germ lines (Van der Putten et al., 1985, Proc. Natl. Acad. Sci. USA 82:6148-6152); gene targeting in embryonic stem cells (Thompson et al., 1989, Cell 56:313-321); electroporation of embryos (Lo, 1983, Mol. Cell. Biol. 3:1803-1814); sperm-mediated gene transfer (Lavitrano et al., 1989, Cell 57:717-723); and positive-negative selection as described in U.S. Pat. No. 5,464,764, herein incorporated by reference. For a review of such techniques, see Gordon, 1989, Transgenic Animals, Intl. Rev. Cytol. 115:171-229, which is incorporated by reference herein in its entirety.

Once transgenic animals have been generated, the expression of the recombinant GHP1 product can be assayed utilizing standard techniques. Initial screening can be accomplished by Southern blot analysis or PCR techniques to analyze animal tissues to test whether integration of the GHP1 transgene has occurred. The level of mRNA expression of the GHP1 transgene in the tissues of the transgenic animals can also be assessed using techniques that include, but are not limited to, Northern blot analysis of cell-type samples obtained from the animal, in situ hybridization analysis, and RT-PCR. Samples of GHP1-expressing tissue can also be evaluated immunocytochemically using antibodies specific for the recombinant transgene product (in certain cases, such as "humanized" knockins where the host GHP1 is replaced by its human ortholog, this might include human GHP1-specific antibodies).

4.7.1. The use of GHP1 Polynucleotide Sequences to Diagnose GHP1-Related Disorders Given GHP1's herein disclosed role in modulating blood lipid levels in vivo, GHP1 encoding sequences can be used in hybridization, PCR, and sequencing based assays to identify and diagnose GHP1-related disorders that result from mutant GHP1 sequences, or to quantify levels of GHP1 expression, thus identifying individuals that are at risk for developing GHP1-related disorders. These assays could be in the form of fluorescence or enzyme based in situ hybridization, PCR, or in a preferred embodiment, hybridization probes used to assess gene expression patterns using a microarray or high-throughput "chip" format.

Certain embodiments of the present invention include assays that utilize, among others, GHP1 encoding sequences (and vectors comprising the same), an open reading frame (ORF) encoding a naturally occurring protein having GHP1 activity and that hybridizes to a complement of a GHP1 DNA sequence under highly stringent conditions, as described herein, and encodes a functionally equivalent gene product. Certain assay embodiments contemplate the use of any nucleotide sequences that hybridize to the complement of a nucleotide sequence that encodes GHP1 under moderately stringent conditions, as described herein, yet still encodes a functionally equivalent GHP1 product. Functional equivalents of GHP1 include naturally occurring GHP1 sequences present in other species and mutant GHP1 sequences, whether naturally occurring or engineered (by site directed mutagenesis, gene shuffling, or directed evolution as described in, for example, U.S. Pat. No. 5,837,458, incorporated herein by reference). The invention also includes degenerate (due to the redundancy of the genetic code) nucleic acid variants of the GHP1 polynucleotide sequences.

Additionally contemplated are certain embodiments that use polynucleotides encoding GHP1 ORFs, or their functional equivalents, encoded by polynucleotide sequences that are about 99, 95, 90, or about 85 percent similar or identical to the GHP1 nucleotide sequences (as measured by BLAST sequence comparison analysis using, for example, the University of Wisconsin GCG sequence analysis package using standard default settings).

In certain embodiments, the invention also includes the use of nucleic acid molecules, preferably DNA molecules, that hybridize to, and are therefore the complements of, the described GHP1 nucleotide sequences. Such hybridization conditions can be highly stringent or less highly stringent, as described herein. In instances where the nucleic acid molecules are deoxyoligonucleotides ("DNA oligos"), such molecules are generally about 16 to about 100 bases long, or about 20 to about 80 bases long, or about 34 to about 45 bases long, or any variation or combination of sizes represented therein that incorporate a contiguous region of GHP1 sequence. Such oligonucleotides can be used, for example, in conjunction with the polymerase chain reaction (PCR) to screen libraries, isolate clones, and prepare cloning and sequencing templates, etc.

For oligonucleotide probes, highly stringent conditions can typically refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). Oligonucleotides of the invention can be synthesized by standard methods known in the art, e.g., by use of an automated DNA synthesizer (such as are commercially available from Biosearch, Applied Biosystems, etc.). As examples, phosphorothioate oligonucleotides can be synthesized (Stein et al., 1988, Nucl. Acids Res. 16:3209), and methylphosphonate oligonucleotides can be prepared by use of controlled pore glass polymer supports (Sarin et al., 1988, Proc. Natl. Acad. Sci. USA 85:7448-7451), etc.

Low stringency conditions are well-known to those of skill in the art, and will vary predictably depending on the specific organisms from which the library and the labeled sequences are derived. For guidance regarding such conditions see, for example, Sambrook et al., 1989, supra; and Ausubel et al., 1989, supra (and periodic updates thereof).

Alternatively, GHP1 oligonucleotides and/or amino acids can be used as hybridization probes for screening libraries, or assessing gene expression-patterns (particularly using a microarray or high-throughput "chip" format). Such assays would be applicable to the screening of large databases containing, for example, sequences obtained from patients suspected of having a GHP1 defect. This methodology would therefore link functional information with large amounts of genetic information.

Additionally, a series of the described oligonucleotide sequences, or the complements thereof, can be used to represent all or a portion of the GHP1 sequences. An oligonucleotide, polynucleotide, or amino acid sequence of GHP1 can also be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence of GHP1 or the amino acid sequence encoded thereby. Methods for attaching biopolymers to, or synthesizing biopolymers on, solid support matrices, and conducting binding studies thereon, are disclosed in, inter alia, U.S. Pat. Nos. 5,700,637, 5,556,752, 5,744,305, 4,631,211, 5,445,934, 5,252,743, 4,713,326, 5,424,186, and 4,689,405, the disclosures of which are herein incorporated by reference in their entirety.

Addressable arrays comprising sequences from GHP1 can also be used to identify and characterize the temporal and tissue specific expression of GHP1. These addressable arrays incorporate oligonucleotide sequences of sufficient length to confer the required specificity, yet be within the limitations of the production technology. The length of these probes is within a range of between about 8 to about 2000 nucleotides (or any whole number within the stated range) in length, and can partially overlap each other and/or the sequence may be represented using oligonucleotides that do not overlap. Preferably the probes consist of about 60 nucleotides or at least about 25 nucleotides from a GHP1 sequence.

For example, a series of GHP1 oligonucleotide sequences, or the complements thereof, can be used in chip format to represent all or a portion of a GHP1 sequence. The oligonucleotides, typically between about 16 to about 40 (or any whole number within the stated range) nucleotides in length, can partially overlap each other and/or the sequence may be represented using oligonucleotides that do not overlap. Accordingly, the described polynucleotide sequences should typically comprise at least about two or three distinct oligonucleotide sequences of at least about 8 nucleotides in length of GHP1 sequence. Such oligonucleotide sequences can begin at any nucleotide present within a GHP1 sequence and proceed in either a sense (5'-to-3') orientation vis-a-vis the described sequences or in an antisense (3'-to-5') orientation.

Microarray-based analysis allows the discovery of broad patterns of genetic activity, providing new understanding of gene functions and generating novel and unexpected insight into transcriptional processes and biological mechanisms. The use of addressable arrays comprising GHP1 sequences can provide detailed information about GHP1 transcriptional changes involved in a specific pathway, potentially leading to the identification of novel components or gene functions that manifest themselves as novel phenotypes.

As a further example of utility, GHP1 sequences can be utilized in microarrays or other assay formats to screen collections of genetic material from patients that have a GHP1-related disorder. These investigations can be carried out using GHP1 sequences in silico, and by comparing previously collected genetic databases and the disclosed sequences using conventional computer software known in the art. Thus GHP1 sequences can be used to identify mutations associated with an GHP1-related disease, and also in diagnostic or prognostic assays.

Once a mutant GHP1 sequence has been identified, it can be subject to further DNA sequence analysis. By comparing the DNA sequence of the mutant GHP1 allele to that of a corresponding normal GHP1 allele, the mutation(s) responsible of the alteration of function of the mutant GHP1 product can be ascertained.

4.7.2. GHP1 Proteins and Polypeptides

GHP1 proteins, peptide fragments therefrom, mutated, truncated or deleted forms of GHP1 fusion proteins can be prepared for a variety of uses, including but not limited to, the generation of antibodies, as reagents in diagnostic assays, the identification of other cellular gene products interacting with GHP1 that can further characterize GHP1-related disorders.

GHP1 polypeptides, and corresponding peptides, can be chemically synthesized (e.g., see Creighton, 1983, Proteins: Structures and Molecular Principles, W.H. Freeman & Co., N.Y.); however, larger polypeptides employing GHP1 encoding sequences (full length GHP1, fusion proteins, etc.) can be advantageously produced by recombinant DNA technology using techniques well known in the art for expressing nucleic acids encoding GHP1 sequences and/or coding sequences. Such methods can be used to construct expression vectors containing the GHP1 nucleotide sequence(s) described above and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, RNA corresponding to all or a portion of a transcript encoding a GHP1 nucleotide sequence can be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems can be utilized to express GHP1 encoding nucleotide sequences. Purification or enrichment of GHP1 from such expression systems can be accomplished using appropriate detergents and lipid micelles and methods well known to those skilled in the art. However, such engineered host cells themselves may be used in situations where it is important not only to retain the structural and functional characteristics of GHP1, but to assess biological activity, e.g., in drug screening assays.

Expression systems that can be used for purposes of the invention include, but are not limited to, microorganisms such as bacteria (e.g., *E. coli, B. subtilis*) transformed with recombinant bacteriophage DNA, plasmid DNA or cosmid DNA expression vectors containing GHP1 encoding nucleotide sequence; yeast (e.g., *Saccharomyces, Pichia*) transformed with recombinant yeast expression vectors containing GHP1 encoding nucleotide sequence; insect cell systems infected with recombinant virus expression vectors (e.g., baculovirus) containing GHP1 encoding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing GHP1 encoding nucleotide sequence; or mammalian cell systems (e.g., COS, CHO, BHK, 293, 3T3, etc.) harboring recombinant expression constructs containing promoters derived from the genome of mammalian cells (e.g., metallothionein promoter) or from mammalian viruses (e.g., the adenovirus late promoter; the vaccinia virus 7.5K promoter, etc.).

In bacterial systems, a number of expression vectors can be advantageously selected depending upon the use intended for the product being expressed. Vectors that direct the expression of high levels of fusion protein products that are readily purified can be desirable to, for example, produce large quantities of protein for the generation of pharmaceutical compositions comprising GHP1 protein, or for raising antibodies to GHP1 protein, or corresponding inhibiting peptides. Such vectors include, but are not limited to, the *E. coli* expression vector pUR278 (Ruther et al., 1983, EMBO J. 2:1791), in which a GHP1 encoding sequence can be ligated individually into the vector in frame with the lacZ coding region so that a fusion protein is produced; pIN vectors (Inouye & Inouye, 1985, Nucleic Acids Res. 13:3101-3109; Van Heeke & Schuster, 1989, J. Biol. Chem. 264:5503-5509); and the like. PGEX vectors can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhidrosis virus (AcNPV) is used as a vector to express foreign genes. The virus grows in *Spodoptera frugiperda* cells. The GHP1 coding sequence can be cloned into non-essential regions (for example the polyhedrin gene) of the virus and placed under control of an AcNPV promoter (for example the polyhedrin promoter). Successful insertion of GHP1 coding sequence will result in the inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, GHP1-encoding nucleotide sequence can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing GHP1 in infected hosts (e.g., See Logan & Shenk, 1984, Proc. Natl. Acad. Sci. USA 81:3655-3659). Similar vectors can be used to deliver GHP1 in vivo via gene delivery of GHP1 encoding polynucleotides, or to deliver nucleotide based antagonists of GHP1 expression (i.e., antisense or ribozyme inhibitors of GHP1 expression).

Specific initiation signals can also be required for efficient translation of inserted GHP1-encoding sequences. These signals include the ATG initiation codon and adjacent sequences. In cases where an entire GHP1 encoding sequence or cDNA, including its own initiation codon and adjacent sequences, is inserted into the appropriate expression vector, no additional translational control signals may be needed. However, in cases where only a portion of the GHP1 coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (See Bitter et al., 1987, Methods in Enzymol. 153:516-544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, and in particular, hypothalamus cell lines.

For long-term, high-yield production of recombinant proteins, stable expression is preferred. For example, cell lines that stably express GHP1 can be engineered. Rather than using expression vectors that contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines that express GHP1. Such engineered cell lines can be particularly useful in screening and evaluation of compounds that affect the endogenous activity GHP1.

A number of selection systems can be employed in the practice of certain embodiments of the present invention, including, but not limited to, herpes simplex virus thymidine kinase (Wigler, et al., 1977, Cell 11:223), hypoxanthine-guanine phosphoribosyltransferase (Szybalski & Szybalski, 1962, Proc. Natl. Acad. Sci. USA 48:2026), and adenine phosphoribosyltransferase (Lowy, et al., 1980, Cell 22:817) genes can be employed in tk-, hgprt- or aprt-cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colbere-Garapin, et al., 1981, J. Mol. Biol. 150:1); and hygro, which confers resistance to hygromycin (Santerre, et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972-8976). In this system, the gene of interest is subcloned into a vaccinia recombination plasmid such that the gene's open reading frame is translationally fused to an amino-terminal tag consisting of six histidine residues.

Extracts from cells infected with recombinant vaccinia virus are loaded onto Ni2+ nitriloacetic acid-agarose columns and histidine-tagged proteins are selectively eluted with imidazole-containing buffers.

In certain additional embodiments, GHP1 proteins can be produced by gene activation (see generally U.S. Pat. Nos. 5,968,502 and 6,524,818) and/or introduced using cells that have been modified ex vivo to activate GHP1 production.

In certain additional embodiments phospholipase resistant "anchors" can be attached to GHP1 to enhance the molecules persistence on the cell surface or for formulation with normally GPI-anchored forms of GHP1 to enhance the in vivo characteristics of GHP1.

5. EXAMPLES

5.1. Mouse Care and Dietary Studies

Mouse studies were performed according to federal guidelines. Mice were housed at 24° C. on a fixed 12 hour light/12 hour dark cycle and had ad libitum access to water and rodent chow (22% calories from fat) (product no. 5001; Purina, St. Louis, Mo.) or high fat diet (HFD, 60% calories from fat) (product no. D12492; Research Diets, New Brunswick, N.J.) as indicated below. Mice that were fed HFD received that diet from the age of 4-5 weeks onward. Mice referred to below as being in the "fasted state" were deprived of food for 16 hours.

5.2. GHP1 Gene Disrupted Mice

The entire coding region (coding exons 1-4) of the murine GPH1 gene (see GenBank Accession Number BC061225) was removed by homologous recombination, generally as described in U.S. Pat. Nos. 5,487,992, 5,627,059, and 5,789,215, and U.S. patent application Ser. No. 09/171,642, filed Oct. 21, 1998, each of which are hereby incorporated herein by reference in their entirety. The resulting knock-out animals displayed a notable increase in serum cholesterol, triglyceride and total bilirubin levels, and a notable decrease in serum calcium, sodium and chloride levels. These data, taken together with the data below, indicate that administration of GHP1-related or associated disorders and diseases.

5.3. The Effect of GHP1 Disruption on Mouse Physiology

Mice homozygous (−/−) for the disruption of the GHP1 gene were studied in conjunction with mice heterozygous (+/−) for the disruption of the GHP1 gene, and wild-type (+/+) litter mates. During this analysis, the mice were subject to a medical work-up using an integrated suite of medical diagnostic procedures designed to assess the function of the major organ systems in a mammalian subject. By studying the homozygous (−/−) "knockout" mice in the described numbers and in conjunction with heterozygous (+/−) and wild-type (+/+) litter mates, more reliable and repeatable data were obtained. Disruption of the GHP1 gene, which was confirmed by Southern analysis, resulted in notable differences in blood chemistry, hematology, immune status, opthalmology, pathology, and radiology, as described in greater detail below.

Expression of the murine homolog of GHP1 was detected by RT-PCR in murine spinal cord, thymus, spleen, lung, kidney, liver, stomach, small intestine and colon, heart, adipose, asthmatic lung, LPS liver, blood, banded heart, aortic tree, prostate, and mammary gland (5 week virgin, mature virgin, 12 DPC, 3 day post-partum (lactating), 3 day post-weaning (early involution), and 7 day post-weaning (late involution)).

5.3.1. The Effect of GHP1 Disruption on Blood Chemistry

Approximately 200 microliters of whole blood was collected from the retro orbital plexus. The blood was placed in a 2.5 ml micro-collection tube and centrifuged to obtain the serum. The sample was analyzed for the following analytes: albumin, alkaline phosphatase, alanine aminotransferase (ALT), total bilirubin, blood urea nitrogen (BUN), calcium, glucose, phosphorus, potassium, sodium, chloride, cholesterol, triglycerides, uric acid and creatinine using a Cobas Integra 400 (Roche Diagnostics). The Cobas Integra 400 is a random and continuous access, sample selective analyzer. The analyzer uses four measuring principles: absorbance photometry, turbidimetry, fluorescence polarimetry and ion-selective electrode potentiometry to assay the analytes described above.

Eight (8) homozygous (−/−) mice (four (4) males and four (4) females), four (4) heterozygous (+/−) mice (two (2) males and two (2) females), and four (4) wild-type (+/+) mice (two (2) males and two (2) females) were analyzed. There were a number of significant differences observed in the blood chemistry analysis that could be attributed to differences in GHP1 expression, as detailed below.

The total serum cholesterol levels were significantly increased in the homozygous (−/−) animals. The total serum cholesterol levels of the homozygous (−/−) animals was 489.0 mg/dL±148.1 mg/dL, compared to 161.0 mg/dL±21.2 mg/dL for the heterozygous (+/−) animals and 118.5 mg/dL±9.8 mg/dL for the wild-type (+/+) animals. This difference was noted in both male and female animals, with the male homozygous (−/−) animals having total serum cholesterol levels of 489.0 mg/dL±119.9 mg/dL, compared to 165.5 mg/dL±19.1 mg/dL for the male heterozygous (+/−) animals and 118.5 mg/dL±9.2 mg/dL for the male wild-type (+/+) animals, and the female homozygous (−/−) animals having total serum cholesterol levels of 435.0 mg/dL±148.2 mg/dL, compared to 150.5 mg/dL±27.6 mg/dL for the female heterozygous (+/−) animals and 121.0 mg/dL±14.1 mg/dL for the female wild-type (+/+) animals.

The total serum triglyceride levels were also significantly increased in the homozygous (−/−) animals. The total serum triglyceride levels of the homozygous (−/−) animals was 6,635.0 mg/dL±3,088.5 mg/dL, compared to 89.0 mg/dL±55.3 mg/dL for the heterozygous (+/−) animals and 85.0 mg/dL±70.7 mg/dL for the wild-type (+/+) animals. This difference was also noted in both male and female animals, with the male homozygous (−/−) animals having total serum triglyceride levels of 7,626.5 mg/dL±2,681.0 mg/dL, compared to 141.0 mg/dL±45.3 mg/dL for the male heterozygous (+/−) animals and 157.0 mg/dL±75.0 mg/dL for the male wild-type (+/+) animals, and the female homozygous (−/−) animals having total serum triglyceride levels of 5,671.5 mg/dL±2,636.4 mg/dL, compared to 58.0 mg/dL±15.6 mg/dL for the female heterozygous (+/−) animals and 60.5 mg/dL±7.8 mg/dL for the female wild-type (+/+) animals.

The total serum bilirubin levels were also significantly increased in the homozygous (−/−) animals. The total serum bilirubin levels of the homozygous (−/−) animals was 8.04 mg/dL±4.30 mg/dL, compared to 0.33 mg/dL±0.18 mg/dL for the heterozygous (+/−) animals and 0.28 mg/dL±0.23 mg/dL for the wild-type (+/+) animals. However, the notable lipemia in the homozygous (−/−) animals could have skewed the total serum bilirubin reading, since the presence of even slight lipemia is known to affect the reliability of serum bilirubin measurements.

The total serum calcium, sodium, and chloride levels were decreased in the homozygous (−/−) animals. The total serum calcium levels of the homozygous (−/−) animals was 5.8 mg/dL±1.1 mg/dL, compared to 10.2 mg/dL±0.4 mg/dL for the heterozygous (+/−) animals and 9.7 mg/dL±0.3 mg/dL for the wild-type (+/+) animals. The total serum sodium levels of the homozygous (−/−) animals was 135.8 mg/dL±6.0 mg/dL, compared to 146.1 mg/dL±1.1 mg/dL for the heterozygous (+/−) animals and 146.5 mg/dL±0.4 mg/dL for the wild-type (+/+) animals. The total serum chloride levels of the homozygous (−/−) animals was 100.7 mg/dL±5.6 mg/dL, compared to 111.7 mg/dL±1.4 mg/dL for the heterozygous (+/−) animals and 111.0 mg/dL±0.7 mg/dL for the wild-type (+/+) animals.

There was no significant difference in the albumin, alkaline phosphatase, alanine aminotransferase (ALT), blood urea nitrogen (BUN), glucose, phosphorus, potassium, uric acid and creatinine levels between groups (either in the males or the females).

HgbA1C levels were determined in eight (8) homozygous (−/−) mice (four (4) males and four (4) females) and four (4) wild-type (+/+) mice (two (2) males and two (2) females). The anticoagulated whole blood specimen is either manually (Hgb %) or automatically (A1c %) hemolyzed. The released hemoglobin is determined on the Cobas Integra 400 in the hemolysate. HgbA1c is then measured using monoclonal antibodies attached to latex particles. The final result is expressed as either percent HgbA1c (automatic hemolysis) or percent Hgb (manual hemolysis) and is a calculated value.

No notable difference was seen in the levels of HgbA1C in the homozygous and wild-type mice.

5.3.2. The Effect of GHP1 Disruption on Hematology

Whole blood was collected by retro orbital bleed and placed in a capillary blood collection tube that contained EDTA. The blood was analyzed using the Cell-Dyn 3500R analyzer (Abbott Diagnostics). The analyzer employs dual technologies to provide the basis for a five-part white blood cell (WBC) differential identification. Multi-Angle Polarized Scatter Separation (M.A.P.S.S.) provides the primary white blood cell count and differential information, while impedance provides additional information in the presence of fragile lymphocytes and hypotonically resistant red blood cells. Approximately 135 microliters of whole blood is aspirated into the analyzer using a peristaltic pump. Four independent measurement techniques are used by the Cell-Dyn 3500R System (Abbott, Ill.) to obtain the hematologic parameters. The WBC Optical Count (WOC) and the WBC differential data are measured in the optical flow channel, resulting in the identification of the WBC subpopulations (neutrophils, lymphocytes, monocytes, eosinophils, and basophils) for the five part WBC differential. The WBC Impedance Count (WIC) is measured in one electrical impedance channel. The RBC and platelet data are measured in a second electrical impedance channel. The hemoglobin is measured in the spectrophotometric channel. The sample was aspirated, diluted, mixed, and the measurements for each parameter are obtained during each instrument cycle. The final hematological analysis parameters obtained are white blood cell count, neutrophils, lymphocytes, monocytes, eosinophils, basophils, red blood cells, hemoglobin, hematocrit, mean corpuscular volume, mean corpuscular hemoglobin, mean corpuscular hemoglobin concentration, platlets, red cell distribution width and mean platelet volume.

Blood samples were obtained from a total of eight (8) homozygous (−/−) mice (four (4) males and four (4) females), four (4) heterozygous (+/−) mice (two (2) males and two (2) females) and four (4) wild-type (+/+) mice (two (2) males and two (2) females). There were a number of significant differences observed in the hematology analysis that could be attributed to differences in GHP1 expression, as detailed below.

The mean absolute neutrophil count was increased in the homozygous (−/−) animals, while the mean absolute lymphocyte count, the mean red blood cell count, and the mean hematocrit level were decreased in the homozygous (−/−) animals. The mean absolute neutrophil count in the homozygous (−/−) animals was 4.83+2.41, compared to 0.64±0.28 for the heterozygous (+/−) animals and 0.67±0.40 for the wild-type (+/+) animals. The mean absolute lymphocyte count in the homozygous (−/−) animals was 2.15±2.62, compared to 6.33±2.14 for the heterozygous (+/−) animals and 5.47±3.41 for the wild-type (+/+) animals, and the mean red blood cell count in the homozygous (−/−) animals was 8.8±1.0, compared to 10.0±0.1 for the heterozygous (+/−) animals and 9.9+0.3 for the wild-type (+/+) animals. The mean hematocrit level in the homozygous (−/−) animals was 39.7±3.0, compared to 43.0±1.4 for the heterozygous (+/−) animals and 42.0±0.5 for the wild-type (+/+) animals.

The mean corpuscular volume, mean corpuscular hemoglobin, mean corpuscular hemoglobin concentration, and red blood cell distribution width were all increased in the homozygous (−/−) animals. The mean corpuscular volume in the homozygous (−/−) animals was 45.5±2.2, compared to 42.7±0.8 for the heterozygous (+/−) animals and 42.1±1.6 for the wild-type (+/+) animals. The mean corpuscular hemoglobin in the homozygous (−/−) animals was 18.0±1.9, compared to 14.9±0.2 for the heterozygous (+/−) animals and 15.1±0.6 for the wild-type (+/+) animals. The mean corpuscular hemoglobin concentration in the homozygous (−/−) animals was 39.5±3.4, compared to 34.9±0.3 for the heterozygous (+/−) animals and 35.7±0.5 for the wild-type (+/+) animals. The red blood cell distribution width in the homozygous (−/−) animals was 21.4±2.2, compared to 16.9±0.7 for the heterozygous (+/−) animals and 17.3±1.1 for the wild-type (+/+) animals.

There was no significant difference in the white blood cell count, monocytes, eosinophils, basophils, hemoglobin, platlets, and mean platelet volume levels between groups (either in the males or the females).

5.3.3. The Effect of GHP1 Disruption on Immune Status

The acute phase response assay was used to assess the immune system of four (4) homozygous (−/−) male mice and four (4) wild-type (+/+) male mice by challenge with bacterial lipopolysaccharide (LPS). LPS is an endotoxin, and a potent inducer of the acute phase response and systemic inflammation. Briefly, mice were injected intraperitoneally (IP) with sublethal dose of LPS in 200 µl of sterile saline using a 26 gauge needle. The dose was based on the average weight of the mice tested at 1 µg/g body weight. Three hours after injection, a 100 µl blood sample was taken and analyzed for the presence of TNFα(, MCP-1, interferon-g, IL-6, IL-10 and IL-12p70 by flow cytometric analysis.

The homozygous (−/−) mice exhibited a significantly increased mean serum IL-6 level (139,950+44,242 µg/ml) after LPS challenge when compared with their wild-type (+/+) litter mates (42,748+8,019 pg/ml). No notable difference between the homozygous and wild-type animals was seen in any of the other parameters.

Additionally, the levels of soluble intracellular adhesion molecule-1 (sICAM-1) were measured 3 hours after the injection of the mice with the sub lethal dose of LPS. Intracellular adhesion molecule-1 is an inducible transmembrane molecule that plays a role in cell migration, antigen presentation and leukocyte activation. The mouse sICAM-1 immunoassay is a 4.5 hour solid phase ELISA designed to measure mouse sICAM-1 levels in serum and plasma.

There was no significant difference in the sICAM-1 levels between groups.

5.3.4. The Effect of GHP1 Disruption on Ophthalmology

The effect of the GHP1 disruption on a variety of opthalmological parameters was analyzed, as detailed below.

Slit Lamp Analysis: The slit lamp is a biomicroscope that allows examination of the anatomy of the anterior eye segment as well as the localization of some abnormalities. It is a rapid and convenient method for preliminary eye examination prior to fundus photography. Mouse eye analysis began with examination utilizing a slit lamp (Nikon, Tokyo, Japan) in combination with a 60 or 90 diopter (D) condensing lens. In preparation for examination, mouse pupils were dilated by adding a drop of 1% cyclopentolate and 1% atropine (Alcon Laboratory Inc., Fort Worth, Tex.) to each eye.

Fundus Photography: Fundus photography is a noninvasive method of examining the eye that is adaptable to high throughput analysis. The appearance of the ocular fundus is representative of overall health. Variation in the appearance of the ocular fundus can be indicative of different diseases, including, but not limited to, diabetes, obesity, cardiovascular disorders, angiogenesis, oxidant related disorders and cancer. Selected animals were subjected to fundus photography using a Kowa Genesis small animal fundus digital camera (Tokyo, Japan) to photograph mouse fundi. The instrument was used with a condensing lens, Volk 60D or 90D (Mentor, Ohio, USA), mounted between the camera and the object to be viewed (mouse eye). In order to avoid complications of anesthesia, such as clouding of the ocular media, photographs were obtained on conscious mice, whose vibrissae were trimmed with fine scissors to prevent them from obscuring the photograph.

Retinal Angiography: Fluorescein angiography is an established technique used to examine the circulation of the retina. In particular it enables the progression of diabetic retinopathy to be monitored and provides valuable information on the presence or absence of vascular lesions such as edema (leakage) and ischemia (occlusion of the capillaries). The retinal angiography procedure was similar to the procedure used for fundus photography, except that the standard light was replaced with blue light in combination with a barrier filter. To facilitate imaging mice were injected intraperitoneally with 25% sodium fluorescein (Akorn Inc., Decator, Ill.) at a dose of 0.01 ml per 5-6 gm body weight. For viewing, the eyepiece was fitted with the manufacturer-supplied barrier filter. The digital imaging system used consists of a camera, a computer and Komit+software (Kowa, Tokyo, Japan) especially designed for opthalmological applications, and facilitates image data acquisition, analysis and storage.

The artery to vein ratio (A/V) is the ratio of the artery diameter to the vein diameter (measured before the bifurcation of the vessels). The A/V ratio is measured and calculated according to fundus images. Many diseases will influence the ratio, i.e., diabetes, cardiovascular disorders, papilledema and optic atrophy.

Opthalmological analysis was performed on a total of sixteen (16) mice: eight (8) homozygous (−/−) mice (four (4) males and four (4) females); four (4) heterozygous (+/−) mice (two (2) males and two (2) females); and four (4) wild-type (+/+) mice (two (2) males and two (2) females). Fundus examination revealed that the homozygous (−/−) mice all exhibited semi-transparent retinal vessels that appeared pink in color. The bloodstream could be observed under the fundus microscope, suggesting anomalies of the retinal vasculature in the homozygous (−/−) mice.

Analysis of the retinal angiography revealed that the main retinal vasculature of the homozygous (−/−) mice could be clearly visualized with blue light illumination before administration of the fluorescein dye, suggesting increased fluorescent material was already present in the blood of the homozygous (−/−) mice. After administration of the fluorescein dye, no notable difference was observed in the retinal angiograms and the A/V ratio between the homozygous (−/−) mice and their heterozygous (+/−) and wild-type (+/+) litter mates.

5.3.5. The Effect of GHP1 Disruption on Pathology

The effect of the GHP1 disruption on gross and microscopic pathology was determined in a total of nine (9) mice: six (6) homozygous (−/−) mice, one (1) heterozygous (+/−) mouse, and two (2) wild-type (+/+) mice. While no notable differences were observed in gross pathology between the homozygous (−/−), heterozygous (+/−), and wild-type (+/+) mice, microscopic examination revealed that among the six (6) homozygous (−/−) mice examined, four (4) exhibited markedly hyperlipidemic blood at necropsy. Histopathology revealed increased amounts of pale-staining acellular material in scattered blood vessels. In the four (4) homozygous (−/−) mice with lipemia, the only notable histopathologic alteration was in the cytoplasm of all cells in the zona fasciculata of the adrenal gland. Instead of the normal microvacuolated cytoplasm typical of these cells in normal tissue, the cytoplasm of these cells lacked microvacuoles in the four (4) hyperlipidemic homozygous (−/−) mice. Instead, the cytoplasm of the zona fasciculata cells in the four (4) hyperlipidemic homozygous (−/−) mice was uniformly finely granular and eosinophilic, which would be consistent with altered lipid/cholesterol uptake or metabolism in these cells.

5.3.6. The Effect of GHP1 Disruption On Radiology

Three (3) homozygous (−/−) mice (two (2) males and one (1) female), two (2) heterozygous (+/−) mice (one (1) male and one (1) female), and one (1) male wild-type (+/+) mouse were examined using a mouse-size computer aided tomography (CT) scanning unit, the MicroCAT™ (ImTek, Inc., Knoxyille, Tenn.). The mice were injected with a CT contrast agent, Omnipaque 300 (Nycomed Amersham, 300 mg of iodine per ml, 0.25 ml per animal, or 2.50-3.75 g iodine/kg body weight), intraperitoneally. After resting in the cage for approximately 10 minutes, the mice were sedated by intraperitoneal injection of Avertin (1.25% 2,2,2,-tribromoethanol, 20 ml/kg body weight). The CT-scan was done with the anesthetized animal lying prone on the test bed. Three dimensional images were reconstructed by the Feldkamp algorithm in a cluster of workstations using ImTek 3D RECON software.

There were no radiologic findings of significance that differentiated the homozygous (−/−) mice from the heterozygous (+/−) or wild-type (+/+) mice. The following observations were made for all groups of mice. There were no abnormalities observed in the skull, spine, tail or individual bones. The head, brain and neck appeared normal. The cervical lymph nodes were not enlarged. The lung fields were clear. The hearts were of normal size. The mediastinum and vessels revealed no abnormalities. The liver, spleen and kidneys were normal in size, shape and position. The rate of excretion of contrast media from the kidneys was within normal limits, indicating normal kidney function. The lymph nodes, and other abdominal organs, such as the adrenals, ovaries and prostate were normal. No lesions were observed in the soft tissues (skin, muscle or fat).

Additionally, a Scanco μCT40 (miniaturized CAT scanner (Scanco USA, Inc., Wayne, Pa.) was used to measure BMD in four (4) male homozygous (−/−) mice and two (2) male wild-type (+/+) mice. The μCT40 scans dissected bones and provides detailed information on bone mass and architecture. Multiple bones are placed into sample holders and scanned automatically. The instrument software is then used to select regions of interest for analysis. Trabecular bone parameters are analyzed in the fifth lumbar vertebrae (LV5) at 16 micrometer resolution and cortical bone parameters are analyzed in the femur midshaft at a resolution of 20 micrometers.

The male homozygous (−/−) mice exhibited increased mean vertebral trabecular number (4.97±0.25/mm) when compared with the male wild-type (+/+) mice (3.78±0.28/mm), and also exhibited increased connectivity density (179.7±25.5/mm3) when compared with the wild-type (+/+) mice (94.3±11.6/mm3).

5.3.7 The Effect of GHP1 Disruption on Blood Pressure

Blood pressure was determined in eight (8) homozygous (−/−) mice (four (4) males and four (4) females) and four (4) wild-type (+/+) mice (two (2) males and two (2) females). Mice were subjected to a conscious systolic blood pressure protocol similar to that previously described (Krege et al., Hypertension 25:1111-1115, 1995). Briefly, mice were placed on a heated platform (37 degrees C.) with their tails placed through a cuff and in a sensor on the Visitech BP-2000 Blood Pressure Analysis System (Visitech Systems, Apex, N.C.) to detect the systolic and diastolic blood pressure. The blood pressure was measured 10 times a day for 4 consecutive days, and then the four days are averaged to obtain the conscious systolic blood pressure.

There was no significant difference in the average systolic blood pressure between groups (either in the males or the females).

5.3.8 The Effect of GHP1 Disruption on Heart Rate

In an additional study, the heart rate was determined in eight (8) homozygous (−/−) mice (four (4) males and four (4) females) and four (4) wild-type (+/+) mice (two (2) males and two (2) females). Briefly, heart rate is measured via a noninvasive tail-cuff method for four days on the Visitech BP-2000 Blood Pressure Analysis System (Visitech Systems, Apex, N.C.). Heart rate is measured ten times each day for four days. The measurements on each of the four days are then averaged to obtain the conscious heart rate.

There was no significant difference in the average heart rate between groups (either in the males or the females).

5.3.9 The Effect of GHP1 Disruption on Size, Percent Body Fat, and Bone Mineral Density Body composition and percent body fat was measured by dual energy X-ray absorptiometry (DEXA) using the Piximus small animal densitometer (Lunar Corporation, Madison, Wis.). Individual mice were sedated with Avertin (1.25% solution, 2.5 mg/10 gm body weight delivered by intraperitoneal injection), immobilized on a positioning tray and then placed on the Piximus imaging window. All scans were performed using the total body mode (0.18×0.18 mm), and the analysis was performed on the total body region of interest. The entire body, except the head, of each mouse was exposed for 5 minutes to a cone shaped beam of both high and low energy x-rays. A high-resolution digital picture was taken of the image of the x-rays hitting a luminescent panel. Lunar PIXImus software (version 1.45) was used to calculate the ratio of attenuation of the high and low energies to separate bone from soft tissue compartments and, within the soft tissue compartment, to separate lean tissue mass from fat mass and thus determine the bone mineral density (BMD), total bone mineral content (BMC), fat composition (% fat), lean body mass (LBM) and total tissue mass (TTM) in the regions of interest (total body for all tests, and additionally, vertebrae and both femurs for BMD). Previous studies have determined that this technique precisely measures fat and lean tissue mass, and that there is a close relationship between fat and lean tissue mass estimated by this technique with those measured using chemical carcass analysis (Nagy and Clair, Obesity Research 8:392-398, 2000). DEXA measurements of body fat weight are closely correlated with measurements of body fat weight as determined by carcass analysis (Brommage, Am. J. Physiol. Endocrinol. Metab. 285:E454-E459, 2003). The volumetric bone mineral density (VBMD) was also calculated. Volumetric bone mineral density is a mathematical adjustment made to correct for error introduced when a 3 dimensional value (density) is calculated from 2-dimensional data (DEXA readout).

Body composition and percent body fat was measured in eight (8) homozygous (−/−) mice (four (4) males and four (4) females), four (4) heterozygous (+/−) mice (two (2) males and two (2) females), and four (4) wild-type (+/+) mice (two (2) males and two (2) females). There was no notable difference between groups (either in the males or the females) in TTM, LBM, % fat, grams of fat (TTM×% fat/100), total body BMD, femur BMD, vertebrae BMD, vBMD, total body BMC, and BMC/LBM.

Mouse body weight was determined to the nearest 0.1 gm using an Ohaus Scout scale. Body length was determined from nose to the base of tail and is reported in cm. Body weight and body length data were obtained for mice at eight (8) weeks of age. The body weight was measured in eight (8) homozygous (−/−) mice (four (4) males and four (4) females), four (4) heterozygous (+/−) mice (two (2) males and two (2) females), and four (4) wild-type (+/+) mice (two (2) males and two (2) females). There was no notable difference in body weight between groups (either in the males or the females).

Body length data was measured in eight (8) homozygous (−/−) mice (four (4) males and four (4) females), four (4) heterozygous (+/−) mice (two (2) males and two (2) females), and four (4) wild-type (+/+) mice (two (2) males and two (2) females). There was no notable difference in body length between groups (either in the males or the females).

5.3.10. The Effect of GHP1 Disruption on Mononuclear Cell Profiles

Peripheral blood leukocytes were tested for cell surface differentiation marker expression by FACS analysis.

Aliquots of cells corresponding to $2-4 \times 10^5$ cells were washed and suspended in ice-cold phosphate-buffered saline solution, containing 0.1% bovine serum albumin and 0.1% sodium-azide (PBS-BSA), and incubated with Fc-block solution (Becton-Dickinson, Sunnyvale, Calif.) to decrease Fc receptor-mediated unspecific antibody binding. After 15 min incubation at 4 degrees C., a mixture of conjugated anti-mouse monoclonal antibodies were added. Negative control samples contained cells incubated with isotype-matched irrelevant monoclonal antibodies. After 30 min incubation with the antibodies in the dark, at 4 degrees C. on ice, the cells were washed three times with PBS-BSA, and resuspended in 300 ml PBS, supplemented with 1% paraformaldehyde. Live cells, 104 per sample, were collected on a FACSCalibur® Cytometer (Becton-Dickinson), and analyzed with Cell Quests software (Becton-Dickinson) for percentage of different leukocyte cell subsets Staining with CD45 identified cells as leukocytes, while granulocytes were excluded by scatter. T cells were identified by the positive expression of TCRb-chain. T cells were further divided into CD4 positive CD8 negative ($CD4^+CD8^-$) mature helper T cells or CD4 negative CD8 positive ($CD4^-CD8^+$) mature cytotoxic/suppressor T cells. Natural Killer (NK) cells and B cells were identified from the TCRb negative (non T-cell) population by staining with pan-NK and CD19 antibody, respectively. Monocytes were defined by gating on forward and side scatter and by staining with monoclonal antibodies to CD45, they are $CD45^+$ mononuclear cells that are negative for all T, B, and NK markers. Antibodies used for this analysis were obtained from Becton-Dickinson and were specifically anti-CD45 antibodies coupled to peridinin chlorophyll protein (PerCP), anti-TCRb-allophycocyanin (APC), anti-CD4-phycoerythrin (PE), anti-CD8 fluorescein isothiocyanate (FITC), anti-pan-NK-PE, and anti-CD19-FITC. The two FITC and PE labeled antibodies stain mutually exclusive cell-types. Granulocytes were defined by their reaction with monoclonal antibody to GR-1. Monocytes were defined as a cell subset that gave positive staining with monoclonal antibody to CD11b, but were negative for GR-1 and other lymphocyte and NK cell-specific markers.

There was no significant difference between groups of mice due to disruption of GHP1 in the percentage of their peripheral blood mononuclear cells that were CD4+ CD8- (mature helper T cells), $CD4^-CD8^+$ (mature cytotoxic/suppressor T cells), NK cells or B cells.

5.3.11. The Effect of GHP1 Disruption on Urinalysis

Approximately 100 microliters of urine was collected by placing mice in a clean cage lined with aluminum foil and carefully watching the mice for urination. Immediately following urination, the sample was collected into a micro-collection tube. The specimen was analyzed using calibrated Chemstrip 101 Urine Analyzer (Ames Diagnostics) urinalysis test strips. The urine was placed on the test pad and was read as indicated by the manufacturer according to the package insert. This urinalysis determines urine osmolality, the presence of leukocytes, nitrite, protein, glucose, ketones, urobilinogen, bilirubin and blood.

Urine samples were obtained from a total of sixteen (16) mice: eight (8) homozygous (−/−) mice (four (4) males and four (4) females), four (4) heterozygous (+/−) mice (two (2) males and two (2) females), and four (4) wild-type (+/+) mice (two (2) males and two (2) females). There was no notable difference in any of the urinalysis parameters between groups (either in the males or the females).

5.3.12. The Effect of GHP1 Disruption on Neurological and Behavioral Analysis Functional Observational Battery (FOB): A subset of tests from the Irwin neurological screen (Irwin, Psychopharmacologia 13:222-257, 1968) were used to evaluate the gross neurological function of the mice. This battery of simple neurological tests took 10 minutes and was useful for detecting severe neurological impairments.

Mice were first examined for their overall physical characteristics, such as presence of whiskers, bald patches, piloerection, exopthalmus, palpebral closure, kyphosis, lordosis, and tail abnormalities. The mice were then placed into an empty cage for one minute. Any abnormal spontaneous behaviors such as wild-running, excessive grooming, freezing behavior, hunched body posture when walking, etc., were recorded. Mice were next placed into an empty cage to assess motor reflexes. The cage was quickly moved side to side and up and down. The normal postural reflex is to extend all four legs in order to maintain an upright, balanced position. The righting reflex was measured by turning the mice on their back and determining how long it took the mice to return to an upright position. Normal mice will immediately right themselves. If a mouse did not right itself within 60 seconds, the mouse was returned to its normal upright position.

The eye blink reflex, ear twitch reflex, and flank reflex were measured by lightly touching the eye, tip of the ear, and torso once each with a thin clear piece of plastic. The whisker-orienting response was measured by lightly touching the whiskers with a thin clear piece of plastic while the animal was allowed to move freely. The whiskers are typically moving. When touched the whiskers of normal mice will stop moving and in many cases the mouse will turn its head to the side where the whiskers were touched. To determine a mouse's visual response to light, the mouse was examined in a dimly lit room. Pupil constriction and dilation reflexes were measured by quickly directing a penlight at the mouse's eye and observing pupil constriction and subsequently pupil dilatation once the light source was removed.

The visual reaching response was measured by suspending a mouse by its tail and moving it down towards the edge of a cage. A mouse that can see the cage will reach towards it when the cage is moved in the direction of the mouse.

The tail suspension response was determined by holding the mouse approximately six inches in the air by the tail for 20 seconds and recording normal behaviors such as grabbing of the hind limbs with the forelimbs and turning up on its sides. If present, abnormal behaviors such as hind limb and forelimb clutch were also recorded.

The cateleptic response was measured by using a small rod at a fixed vertical position. The mouse was positioned such that its forelimbs were resting on the rod. Normal mice in this situation will quickly remove their forelimbs from the rod. A 60 second time limit was allowed, after which a non-responsive mouse was returned to its normal posture.

The olfactory response was tested by using an odor such as vanilla extract as an olfactory cue. A small amount of vanilla was placed on cotton swab and held behind and to the side of a mouse. If the mouse turns and orients itself to the position of the vanilla extract-containing cotton swab, the result is interpreted as an indication that the mouse can smell this olfactory cue.

Mouse body temperature was determined by gently inserting a small probe into the rectum and recording the temperature with a digital read-out (Physitemp, Clifton).

This process took less than 5 sec and the mice appeared calm and unstressed throughout the procedure.

This entire battery of simple neurological tests took about 10 minutes and provided for the detection of severe neurological impairment. At the completion of these tests the mice were returned to their home cage.

Hot Plate Assay for Nociception: Mice were removed from their home cage and placed on a 55.0° C. (+/−0.2° C.) hot plate, and the latency to the first hind limb response was recorded. A Plexiglas enclosure was placed around the subject to keep them from walking off of the plate. The hind paw response is a foot shake, paw lick, or jump. The maximum time allowed for a hind limb response to occur was 30 seconds, after which the mouse was removed if a hind limb response had not occurred.

Open Field Assay for Anxiety Related Responses and Locomotor/Exploratory Activity: Anxiety-related, locomotor, and exploratory responses were measured in a clear Plexiglas (40 cm×40 cm×30 cm) open-field arena. A mouse was placed in the center of the arena and allowed to explore for 20 minutes. Overhead high-level lighting provides additional room lighting to enhance anxiety-related behaviors. Activity in the open field was quantified by a computer-controlled Versamax optical animal activity system (Accuscan Instruments, Columbus, Ohio) containing 16 photoreceptor beams on each side of the arena, thereby dividing the arena into 256 equally-sized squares. An additional set of photobeams was placed above this set to record vertical activity, and a set was placed below to record nose poke activity, thus giving three levels of recordable activity. Total distance traveled (locomotor activity), number of rearing and nose poke events (exploratory activity), and center distance (i.e., the distance traveled in the center of the arena) were recorded. The center distance was divided by the total distance traveled to obtain a center distance:total distance ratio. The center distance:total distance ratio can be used as an index of anxiety-related responses. Data was collected in four-minute intervals over the 20 minute test session.

Inverted Screen Test: The Inverted Screen is used to measure motor strength/coordination. Untrained mice are placed individually on top of a square (7.5 cm×7.5 cm) wire screen which is mounted horizontally on a metal rod. The rod is then rotated 180 degrees so that the mice are on the bottom of the screens. The following behavioral responses are recorded over a 1 min testing session: fell off, did not climb, and climbed up.

Prepulse Inhibition of the Acoustic Startle Response: Prepulse inhibition of the acoustic startle response was measured using the SR-Lab System (San Diego Instruments, San Diego, Calif.). A test session began by placing a mouse in the Plexiglas cylinder where it was left undisturbed for 3 min. A test session consists of three trial types. One trial type was a 40 ms, 120 decibel (dB) sound burst alone that is termed the startle stimulus. There were four different acoustic prepulse plus startle stimulus trial types. The prepulse sound is presented 100 ms before the startle stimulus. The 20 ms prepulse sounds are at 74, 78, 82, and 90 dB. Finally, there were trials where no stimulus is presented to measure baseline movement in the cylinders. Six blocks of the six trial types were presented in pseudorandom order, such that each trial type was presented once within a block of seven trials. The average inter trial interval was 15 sec with a range of 10 to 20 seconds. The startle response is recorded for 65 ms (measuring the response every 1 ms) starting at the onset of the startle stimulus. The background noise level in each chamber is approximately 70 dB. The maximum startle amplitude recorded during the 65 ms sampling window (Vmax) was used.

The formula used to calculate % prepulse inhibition of a startle response is:

$$100-[(\text{startle on acoustic prepulse+startle stimulus trials/startle response alone trials})\times 100].$$

A total of sixteen (16) mice (eight (8) homozygous (−/−) mice (four (4) males and four (4) females) and eight (8) wild-type (+/+) mice (four (4) males and four (4) females)) were analyzed in each of the above tests. There were no notable differences in any of the parameters measured between the groups.

Formalin Paw Test: The formalin paw test is used to assess acute and tonic nociceptive responses in mice. A metal band is placed around the left hind paw of each mouse and 20 ml of 5% formalin is subcutaneously injected in the dorsal surface of the left hind paw. Mice are individually housed in cylindrical chambers for 45 minutes. A computer records flinches per minute, total flinches for phase I (acute phase=first 10 minutes), and total flinches for phase II (tonic phase=last 35 minutes) through an electromagnetic field.

Six (6) homozygous (−/−) mice (three (3) males and three (3) females) and two (2) wild-type (+/+) mice (one (1) male and one (1) female) and were analyzed in the formalin paw test. No notable difference in paw flinching was observed in either phase I or phase II between the two groups.

Circadian Rhythm Analysis: Female mice are individually housed at 4 pm on the first day of testing in 48.2 cm×26.5 cm home cages and administered food and water ad libitum. Animals are exposed to a 12-hour light/dark cycle with lights turning on at 7 am and turning off at 7 pm. The system software records the number of beam interruptions caused by the animal's movements, with beam breaks automatically divided into ambulations. Activity is recorded in 60, one-hour intervals during the three-day test. Data generated are displayed by median activity levels recorded for each hour (circadian rhythm) and median total activity during each light/dark cycle (locomotor activity) over the three-day testing period.

Four (4) female homozygous (−/−) mice and two (2) female wild-type (+/+) mice were analyzed. No notable difference in activity was observed between the groups.

Stress Induced Hyperthermia: Stress-induced hyperthermia (SIH) is a measurement of autonomic hyperactivity induced by anxiety-provoking stimuli. The method involves taking two rectal body temperature measurements 10 minutes apart. SIH is determined by subtracting the basal body temperature (T1) from the stress-enhanced temperature (T2). The difference in delta values (T2−T1=deltaT) indicates the severity of autonomic hyperactivity or SIH. The rise in body temperature associated with SIH is a sign of anticipatory anxiety to the second rectal body temperature measurement. Lower deltaT values suggest decreased anxiety-like responses.

A total of sixteen (16) mice (eight (8) homozygous (−/−) mice (four (4), males and four (4) females) and eight (8) wild-type (+/+) mice (four (4) males and four (4) females)) were analyzed. There was no notable difference between the groups.

Marble Burying: Mice are individually housed in a cage filled with 5 cm of novel bedding for a 30-minute testing period. Up to 16 mice are examined during each testing round. Prior to each round, the experimenter evenly spaces 25 marbles across the bedding surface. After 30-minutes, each mouse is returned to its home cage and all marbles ⅔ buried or more are counted. Borderline marbles (~⅔ buried or less) are not included in the data analysis.

A total of sixteen (16) mice (eight (8) homozygous (−/−) mice (four (4) males and four (4) females) and eight (8) wild-type (+/+) mice (four (4) males and four (4) females)) were analyzed. There was no notable difference between the groups.

Trace Aversive Conditioning: Groups of naive mice are trained in conditioning chambers (Med-Associates, St. Albans, Vt.) that have stainless steel rod floors through which foot shocks are delivered. For cued trace fear conditioning mice are placed in training context and left undisturbed for habituation purposes for 3 minutes. Then a conditioned stimulus (CS: 15 sec duration, 85 dB 3 kHz) generated by tone is delivered, followed by a trace period of 10 sec and the unconditioned stimulus (US: foot shock, 2 sec, 0.5 mA). Mice are presented with 3 trials with inter-trial interval (ITI) 2 minutes and returned to the home cage 1 minute after the final shock.

A total of sixteen (16) mice (eight (8) homozygous (−/−) mice (four (4) males and four (4) females) and eight (8) wild-type (+/+) mice (four (4) males and four (4) females)) were analyzed. There was no notable difference between the groups.

5.3.13 The Effect of GHP1 Disruption on Insulin Levels and Glucose Sensitivity Insulin levels were determined in seven (7) homozygous (−/−) mice (three (3) males and four (4) females) and five (5) wild-type (+/+) mice (three (2) males and two (2) females) by radioimmunoassay (RIA). In RIA, a fixed concentration of labeled antigen (for example, $^{125}$I-insulin) is incubated with a constant dilution of antiserum, such that the concentration of antigen binding sites on the antibody is limited (for example, only 50% of the total labeled antigen concentration may be bound by antibody). When unlabeled antigen (in this example, insulin from serum samples obtained from wild-type and homozygous GHP1 deleted mice) is added, there is competition between labeled and unlabeled antigen for the limited and constant number of binding sites on the antibody. Thus, the amount of labeled antigen bound to the antibody will decrease as the concentration of unlabeled antigen increases. This can be measured after separating antibody-bound from free labeled antigen, and counting either or both fractions. A calibration or standard curve is set up with increasing concentrations of standard unlabeled antigen, and from this curve the amount of insulin in the serum samples can be calculated.

Whole blood was collected retro-orbitally and spun down to collect serum, as described above. The serum was then analyzed for insulin levels utilizing a RIA from Linco (St. Charles, Mo.; Sensitive Rat Insulin RIA Kit, catalog #SRI-13K). This RIA is reported by the manufacturer to be 100% specific (or selective) for mouse insulin, as well as rat insulin I and II. Briefly, the serum (and controls) are incubated with guinea pig anti-rat insulin serum at 4° C. overnight. Then, $^{125}$I-insulin is added to the samples, and then incubated at 4° C. overnight. The samples are then precipitated with goat anti-guinea pig IgG serum, and the amount of labeled insulin in the precipitate was determined using a Cobra II 5000 Series gamma counter (Packard Instrument Company, Inc., Downers Grove, Ill.).

No notable difference was seen in the levels of insulin in the homozygous and wild-type mice.

To determine glucose tolerance, six (6) mice (four (4) homozygous (−/−) mice and two (2) wild-type (+/+) mice, all males) were fasted for 16 hours and then subjected to a standard glucose tolerance test. Briefly, mice were bled (approximately 5 ml) from the tail to determine basal glucose levels using a calibrated Accu-Check Advantage glucometer (Roche Diagnostics Corporation, Indianapolis, Ind.). Mice were then injected with glucose (2 mg/gram body weight), and blood was sampled from the tail at 30, 60, 90 and 120 minutes after the glucose injection to determine glucose levels.

No notable difference was seen in the glucose tolerance responses between the homozygous and the wild-type mice.

5.3.14 The Effect of GHP1 Disruption on Fertility and Reproduction

One (1) male homozygous (−/−) mouse was tested for fertility. The male homozygous (−/−) mouse was bred individually to two wild-type female mice for 14 days (2 females per male). Pregnant females were monitored daily for births, and pup numbers were counted at birth and at post-natal day 4. Pups were monitored daily for milk spots in their stomachs and for growth. Special care was taken not to disturb the litter environment.

The resultant litters were normal in size and occurred in the expected time frame. These data suggest that loss of GHP1 activity apparently has no effect on fertility or mating behavior.

5.3.15 The Effect of GHP1 Disruption on Skin Fibroblast Proliferation and Mammary Gland Development The skin fibroblast proliferation assay uses the increase in the number of cells in a standardized culture as a measure of relative proliferative capacity. Primary fibroblasts are established from skin biopsies taken from wild-type and mutant mice. Duplicate or triplicate cultures of 0.05 million cells are plated and allow to grow for six days. At the end of the culture period, the number of cells present in the culture is determined using a electronic particle counter.

Skin fibroblast proliferation was measured in four (4) female homozygous (−/−) mice and two (2) female wild-type (+/+) mice. No notable difference was seen in the proliferation rate between the fibroblasts isolated from the homozygous and wild-type animals.

Mammary gland development was analyzed in two (2) female homozygous (−/−) mice and one (1) female wild-type (+/+) mouse. Mammary glands will be collected from mice at three times representing distinct stages of development: 1) pre-pubescent virgin (5-6 weeks of age); 2)mid-pregnancy (day 14 post-conception); 3) late involution (day 7 post-weaning).

Ki67 is used to detect cell proliferation in mammary glands taken from mice at mid-pregnancy. This method use formalin-fixation, paraffin-embedding and an anti-Ki67 mAb that detects Ki67 which is cell proliferation marker.

The terminal deoxyribonucleotidyl transferase (TDT)-mediated dUTP-digoxigenin nick end labeling (TUNEL) assay is used to detect DNA fragments in situ, the process that is associated with programmed cell death (apoptosis). The TUNEL assay will be performed on mammary glands at the late involution stage.

After euthanization, the mammary glands are removed, spread on glass microscope slides and fixed overnight in Carnoy's fixative (60% ethanol, 30% chloroform, 10% acetic acid). The glands are then hydrated by sequential 15 minute soaks in 70, 50, and 30% ethanol, followed by a 5 minute soak in distilled water. The glands are then stained overnight in Carmine alum stain. The tissue samples are then dehydrated by sequential 15 minute soaks in 70, 90, 95, and 100% ethanol, cleared overnight in xylene, and mounted with Permount (Fisher Scientific/ProSciTech).

No notable difference was seen in mammary gland development at the young virgin stage between the homozygous and wild-type animals.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims

What is claimed is:

1. A transgenic mouse whose genome comprises a disruption of the GPI-anchored HDL Binding protein 1 (GHP1) gene, wherein said mouse exhibits an increase in serum cholesterol levels when compared to a control mouse.

2. A transgenic mouse according to claim 1, homozygous for said gene disruption, wherein said mouse lacks any expression of GHP1 protein and exhibits hypertriglyceridemia as compared to a control mouse, and wherein the mouse is able to generate antibodies that selectively bind to GHP1.

* * * * *